(12) United States Patent
Mouradian et al.

(10) Patent No.: US 7,588,726 B1
(45) Date of Patent: Sep. 15, 2009

(54) VAPOR ANALYSIS APPARATUS AND METHOD

(75) Inventors: Robert F. Mouradian, Canton, MA (US); Patrick John Kennedy, Pascoag, RI (US); K. Stephen Johnson, Jr., Plymouth, MA (US)

(73) Assignee: Thermo Fisher Scientific Inc., Waltham, MA (US)

( * ) Notice: Subject to any disclaimer, the term of this patent is extended or adjusted under 35 U.S.C. 154(b) by 1092 days.

(21) Appl. No.: 10/617,588

(22) Filed: Jul. 11, 2003

(51) Int. Cl.
*G01N 1/22* (2006.01)
*G01N 21/00* (2006.01)
*G01N 27/00* (2006.01)
*G01N 30/00* (2006.01)

(52) U.S. Cl. .................. 422/83; 422/88; 422/94; 422/95; 422/96; 422/97; 422/98; 436/181; 702/22; 702/23; 702/24; 702/32

(58) Field of Classification Search .................. 422/50, 422/83, 88, 94–98; 436/43, 181; 71/1.01, 71/1.02, 23.2, 23.31, 23.38, 23.36; 702/1, 702/22, 23, 24, 32; 73/1.01, 1.02, 23.2, 23.31, 73/23.38, 23.36
See application file for complete search history.

(56) References Cited

U.S. PATENT DOCUMENTS

| | | | | |
|---|---|---|---|---|
| 1,455,263 A | * | 5/1923 | Oberfell | 73/29.01 |
| 2,743,167 A | * | 4/1956 | Cherry | 422/93 |
| 3,276,241 A | * | 10/1966 | Hubner | 73/23.2 |
| 3,323,350 A | * | 6/1967 | Roberts | 73/40.7 |
| 3,427,862 A | * | 2/1969 | Hubner | 73/23.2 |
| 3,585,845 A | * | 6/1971 | Cornell et al. | 73/40.7 |
| 3,786,675 A | * | 1/1974 | Delatorre et al. | 73/25.03 |
| 3,877,291 A | * | 4/1975 | Hoppesch et al. | 73/23.3 |
| 4,166,380 A | * | 9/1979 | Batz | 73/31.06 |
| 4,173,886 A | * | 11/1979 | Archbold et al. | 73/31.02 |
| 4,323,777 A | * | 4/1982 | Baskins et al. | 250/339.04 |
| 4,443,791 A | * | 4/1984 | Risgin et al. | 340/634 |
| 4,578,586 A | * | 3/1986 | Preston | 250/382 |
| 4,638,443 A | * | 1/1987 | Kaneyasu et al. | 702/24 |

(Continued)

OTHER PUBLICATIONS

Method 21—Determination of Volatile. Organic Compounda Leaks . . . EPA 600/2-81-110, pp. 1151-1166. Sep. 1981.

*Primary Examiner*—Arlen Soderquist
(74) *Attorney, Agent, or Firm*—Chapin IP Law, LLC; Barry W. Chapin, Esq.

(57) ABSTRACT

A vapor analysis system comprising a vapor analyzer capable of collecting and analyzing a vapor sample for detection of a compound that may be contained within the vapor sample. A controller is coupled to the vapor analyzer. The controller is programmed to produce an indicator signal indicative of a relative concentration of the compound detected by the vapor analyzer within the vapor sample. A sample probe includes a housing containing a vapor channel through which the vapor sample is collected, and a vapor cable couples the sample probe to the vapor analyzer to allow collection and channeling of the vapor sample to the vapor analyzer. A multi-dimensional user indicator is disposed on the housing of the sample probe receives and operates in response to the indicator signal to indicate the relative concentration of the compound detected within the vapor sample for presentation via a multi-directional stimulus to a user of the vapor analysis system. Users are able to create user-defined fields in a route entry database and are able to edit route entries while using the vapor analysis system in the field.

29 Claims, 5 Drawing Sheets

U.S. PATENT DOCUMENTS

| | | | |
|---|---|---|---|
| 4,668,940 A * | 5/1987 | Beard et al. | 340/521 |
| 4,670,405 A * | 6/1987 | Stetter et al. | 436/151 |
| 4,786,472 A * | 11/1988 | McConnell et al. | 422/61 |
| 4,879,546 A * | 11/1989 | Dunham et al. | 340/632 |
| 5,068,883 A * | 11/1991 | DeHaan et al. | 378/86 |
| 5,083,019 A * | 1/1992 | Spangler | 250/286 |
| 5,099,437 A | 3/1992 | Weber | |
| 5,206,818 A | 4/1993 | Speranza | |
| 5,214,412 A * | 5/1993 | Gavlak et al. | 340/632 |
| 5,225,996 A | 7/1993 | Weber | |
| 5,351,037 A * | 9/1994 | Martell et al. | 340/632 |
| 5,356,594 A | 10/1994 | Neel et al. | |
| 5,479,359 A | 12/1995 | Rogero et al. | |
| 5,490,413 A * | 2/1996 | Atkinson | 73/40 |
| 5,578,834 A | 11/1996 | Trobridge | |
| 5,889,199 A * | 3/1999 | Wong et al. | 73/40 |
| 5,993,743 A * | 11/1999 | Nordman et al. | 422/94 |
| 6,085,576 A * | 7/2000 | Sunshine et al. | 73/29.01 |
| 6,191,696 B1 * | 2/2001 | Young et al. | 340/632 |
| 6,362,741 B1 * | 3/2002 | Hickox et al. | 340/605 |
| 6,647,761 B2 * | 11/2003 | Barjesteh | 73/40 |
| 6,679,098 B2 * | 1/2004 | Cardinale et al. | 73/23.2 |
| 7,051,577 B2 * | 5/2006 | Komninos | 73/40.5 A |
| 2004/0005715 A1 * | 1/2004 | Schabron et al. | 436/104 |

\* cited by examiner

VAPOR ANALYSIS APPARATUS AND METHOD

FIELD OF THE INVENTION

The present invention generally relates to systems that detect the presence of compounds contained within air or other gas samples and more particularly, to systems that operate as portable gas or vapor measurement systems.

BACKGROUND OF THE INVENTION

Vapor analysis monitoring is an activity that involves detecting and measuring compounds that may be contained within vapor or gas samples collected from a certain region or volume of space. Vapor analysis monitoring is sometimes called "fugitive emissions monitoring" (FEM) and people often use conventional portable vapor analysis monitoring systems as a mechanism to routinely detect chemical leaks from industrial processing equipment such as valves, pipes, flanges, machinery, instrumentation or other equipment installed within industrial facilities such as petroleum refineries, chemical plants, pharmaceutical production facilities, pulp and paper processing facilities and the like. In some of these industries, fugitive emissions monitoring activities are controlled by government regulations that require a systematic approach to identifying and checking hundreds or thousands, and in some cases over one million potential leak points. In many of such industries, vapor analysis monitoring personnel are tasked with continuously checking potential leak points for fugitive emissions (i.e., leaks) on a periodic basis (e.g, daily, weekly, monthly, quarterly, annually). In some instances, a fugitive emissions monitoring program within a large company such as a petroleum processing facility can be a significant operation that employs a dozen or more people on a full-time basis to continuously operate portable vapor analysis system equipment that they transport throughout the company to check for leaks within one or more facilities containing a large number of potential fugitive emissions leak points.

Although the fugitive emissions monitoring industry and computer technology have changed considerably over the last twenty years, the basic measurement technology for concentrations of compounds in gas or vapor samples has been fairly stable. The actual measurement of leaking chemicals or other compounds is made according to procedures published by the United States Environmental Protection Agency (EPA) that are known in the art as "Method 21". The official EPA Method 21 sets basic design and performance requirements for vapor analysis measurement instruments and describes the procedure for making the actual measurement. Method 21 does not specify any particular measurement technology. However, in the 1970s and 1980s, the EPA published a series of studies that evaluated the suitability of several commercially available portable gas and vapor analyzers for use in fugitive emissions monitoring activities. Based on the results of those publications, a portable Flame Ionization Detector (FID) vapor analyzer was identified as the instrument of choice for fugitive emissions monitoring of most organic chemicals and compounds.

Generally, conventional portable gas vapor analysis system equipment includes a pump mechanism coupled via a tubular vapor channel to a hand-held gas sampling probe. In operation, a pump provides a gentle suction or vacuum within the tube and sample probe allowing the user to manually position an inlet of the sample probe nearby a suspected area of fugitive vapor emissions (e.g., next to a suspected leaking valve) in order to draw in and collect an air sample from that region that potentially may contain a compound leaking from that piece of equipment. The pump is configured to channel or distribute that gas sample to a vapor analyzer operating within the portable equipment housing. The vapor analyzer receives the gas vapor sample and uses a Flame Ionization Detector to analyze the gas sample to detect or measure a level or concentration of a suspected compound that may exist within the gas sample. The vapor analysis system can then save (e.g., within an internal memory) and/or output to the user on a display (e.g., LCD) the detected level or concentration of a compound within the vapor sample In 1990, the United States Government enacted the 1990 Clean Air Act Amendments. These amendments phased in a series of new rules that expanded the number of facilities that fall under fugitive emissions monitoring regulation and also increased the frequency of required fugitive emissions monitoring. In addition to the increased monitoring required by state and federal laws since 1990, investigations of many large refineries revealed that many of such facilities were out of compliance. As a result, such facilities currently provide fugitive emissions monitoring programs that operate under court-ordered "consent decrees" which impose even more extensive monitoring requirements.

Previous to the 1990 Clean Air Act Amendments, a two-man team performed most conventional fugitive emissions monitoring. One person handled a portable gas analyzer to check for leaks while the second person carried written instructions for that days work and a clipboard where he or she would record the leak measurement data displayed by the gas analysis system. With the aforementioned expanded monitoring requirements however, recording data by hand was no longer an acceptable option. The manual recording work was simply too slow and labor intensive. In addition, state agencies raised issues of data integrity due to human error or purposeful falsifications introduced by the manual recording process. Accordingly, a new more efficient approach to fugitive emissions monitoring and reporting was required.

A more modern and conventional fugitive emissions monitoring program within a large organization such as a petroleum corporation typically includes a stationary computer system such as a desktop personal computer that operates a specialized and proprietary fugitive emissions data management software application that includes a computerized database organized in a proprietary data format. An example of such a proprietary software application is the Fugitive Emissions Monitoring Software (FEMS) now provided by Essential Information Systems, Inc. The FEMS application (FEMS is a trademark of Essential Information Systems, Inc.) and other third party programs that operate in a similar manner maintain a database listing of all of the potential leak points within a facility along with a set of associated fugitive emissions data such as repair history for each leak point, concentration levels of detected compounds for each leak point, and process conditions associated with those leak points. Generally, as used herein, the term "leak point" is defined as an area, region or volume of space surrounding a piece of equipment such as a valve, pipe flange, coupling, or the like from which a vapor sample needs to be collected and tested for possible fugitive emissions of a compound contained within the vapor sample.

As an example of a typical operation of a fugitive emissions monitoring program, one or more members of a fugitive emissions monitoring team (i.e., employees of the corporation or a team of contracted environmental consultants) connects a conventional portable data logger to a stationary computer system operating the FEMS software in order to upload, into the data logger, a subset of database data referred to as a "route list" or route file containing route entry records defining a set of leak points to be checked for fugitive emissions (i.e. leaks) on that working day. Once the route list is uploaded into the data logger, the team member then begins his or her testing route for the day by transporting the data logger containing the route list and a coupling to a portable gas analyzer out into the facility (i.e., into the field) to check each leak point listed in the route list for possible leakage of compounds such as hydrocarbons that the gas analyzer is configured to detect within collected vapor samples.

As the worker moves through the plant or facility to perform fugitive emissions monitoring, the worker can read the route instructions from the data logger that instruct the worker on the specific location of each leak point to check. Upon arriving at each scheduled leak point defined in the route list, the worker confirms the content of an identification tag associated with that leak point to confirm that the leak point (e.g., a specific valve) is the proper leak point to be tested. Reading the identification of a leak point can be accomplished by having the worker manually enter into the data logger a numeric value or leak point name or identification code displayed on or nearby the leak point. Alternatively, the worker can operate a scanner coupled to the data logger to read a printed bar code label affixed on or nearby the leak point in order to enter the leak point identification into the data logger. In another alternative, the operator can look at the tag and confirm that it matches the expected number shown by the data logger for that leak point.

Once the worker identifies the leak point either manually or via the scanner, the worker uses a handheld probe coupled to the gas analyzer to check for any leaks at that leak point by moving the tip of the probe in sufficiently close proximity to the leak point (e.g., within 2 to 4 inches of a valve) in order to allow the probe of the gas analyzer to collect and channel that vapor sample from that leak point to the vapor analyzer that performs a measurement operation on that vapor sample to determine if the vapor sample contains a specific compound of interest, such as a hydrocarbon. If the gas analyzer indicates that a leak is present at that leak point in an amount that exceeds a predefined threshold (e.g., a certain level or concentration of a hydrocarbon exceeding a certain government rated parts per million level), the worker can enter information into the data logger for that route list entry associated with that leak point in order to identify that leak point as requiring future repair. Alternatively, the worker may perform an immediate repair of the leak point on site, for example, by tightening a valve-packing nut or by performing another repair operation and re-testing the leak point after the repair operation to determine if the leak is still present. The worker can also enter information into the data logger to document the procedure followed for fixing and re-testing this leak point.

Certain conventional gas analyzers also include an embedded computer program that can be configured to associate the scanned bar code label (i.e., the leak point identification) with a concentration value corresponding to a detected concentration of a compound in a vapor sample collected and measured at that leak point by a detector operating within the gas analyzer. In other words, instead of the user having to manually transfer the concentration reading displayed by the gas analyzer into a database within the data logger, some conventional vapor analysis systems include an embedded software program that can capture the detected leak point compound concentration level reading or value and can associate this data to the route list entry associated with the tested leak point.

These more advanced conventional monitoring systems have been manufactured in a variety of configurations to allow a user to upload a route list directly into the gas/vapor measurement systems and then to perform leak detection analysis for leak points. For each route list entry defining a leak point, such conventional systems are capable of associating the concentration reading or level of the detected compound for a particular leak point to the route list entry for that leak point as identified by the leak point identifier. While operating within a facility to detect concentrations of compounds for numerous leak points, such conventional gas vapor analysis systems can store the collected leak concentration levels in each route entry for each leak point and can allow the user to download such information into the proprietary fugitive emissions database software operating within the stationary computer system upon completion of testing leak points associated with each route list entry in the route list for the route on that work day. In other words, more modern conventional portable gas vapor analysis systems are able to perform some of the functions of the data logger related to receiving a route list and associating detected compound concentration levels for each route list entry for each leak point along the route as the user operates the equipment. When the user returns to the central office, the user can connect such conventional gas vapor analysis systems to the stationary computer system and can use the proprietary software application operating in the stationary computer system to extract the concentration data of compounds associated with each leak point that were detected in the field by the gas vapor analysis system.

In particular, one example of a conventional gas vapor analysis system that operates in this manner is the Toxic Vapor Analyzer (e.g., model number TVA-1000) formerly manufactured by The FoxboroCompany, Inc. of Foxboro, Mass., U.S.A. The TVA-1000 features an embedded computer with dedicated software that provides basic vapor detection and data logging capabilities and operates in conjunction with proprietary fugitive emissions database stationary computer software that can upload a route list into the TVA-1000. Another piece of hardware called the "LeakTracker" (LeakTracker is a registered trademark of Tracker Technologies, Inc. DBA Fugitive Emissions Control, Inc.) couples to the TVA-1000 using a proprietary interface cable. This conventional gas vapor analysis system integrates a small hand-held computer, a laser bar code scanner and sample probe for collecting gas vapor samples into one handheld unit. Another conventional gas vapor analyzer system called the HVM-680, manufactured by Thermo Electron Corporation, Inc. of Franklin, Mass., U.S.A., includes an embedded computer system, an integrated laser scanner, a vapor analyzer, and an interface designed specifically for the fugitive emissions market.

SUMMARY OF THE INVENTION

Conventional systems, mechanisms and techniques for performing analysis of compounds that may be contained within vapor samples such as those used in fugitive emissions monitoring programs suffer from a variety of deficiencies. In particular, conventional vapor analysis systems are cumbersome and inefficient to use by workers in the field when performing vapor analysis and leak detection activities for numerous leak points defined in a long route list. Such deficiencies stem from a variety of reasons related to the ergonomic design, construction and functional operation of conventional vapor analysis systems.

As an example, in conventional fugitive emissions monitoring programs that utilize a data logger in conjunction with a gas vapor analysis system, workers that operate such equipment are required to perform a high level of manual interaction to enter concentration data into the data logger for detected concentrations of compounds within gas vapor samples analyzed by the separately operating gas vapor analyzer. Such non-integrated systems allow significant opportunity for human error in this data collection process.

More advanced conventional gas vapor analysis systems provide the user with the ability to upload the route list directly into a vapor analysis system, which can help to avoid some of the error resulting from use of a data logger that is separate and distinct from the vapor analysis system. However, such conventional integrated vapor analysis systems that can receive route list information and that can then associate a detected concentration of a compound to a particular route list entry (i.e., leak point) within the route list without manual data entry still suffer from a variety of operational and design constraints that limit their efficiency in practice.

In particular, such conventional vapor analysis systems that allow uploading of a route list use proprietary and fixed data format for the storage of route list information. As an example, the conventional TVA-1000 and LeakTracker combination gas vapor analysis system uses a rigid, inflexible and proprietary data format for storage of route list entries. This proprietary data format requires that the stationary computer system that uploads the route list into the LeakTracker and that later receives the collected concentration levels for each route list entry be configured to operate a proprietary fugitive emissions monitoring data collection software program (e.g., FEMS) that produces and receives the route list data in a manner that conforms to the proprietary data format of the data logger. Accordingly, since the embedded software within the conventional TVA-1000 system uses a fixed data format, it is difficult if not impossible for a typical user or operator to make modifications to the fugitive emissions application software database format that operates in the stationary computer system.

To illustrate an example of such limitations, the conventional TVA-1000 and Leak Tracker system combination does not provide the ability to allow a user to make significant modifications or customizations to data stored in the LeakTracker, such as route list fields and does not support custom screen or display layout definitions. Nor do such conventional systems support the ability of the user to log comments concerning leak points during field operation or testing.

Furthermore, such proprietary database and record formats and software program operation prevent conventional vapor analysis systems such as the TVA-1000 and LeakTracker systems from operating the stand-alone computer system with third party fugitive emissions data collection software programs that use a different data format. Thus operators are limited by the functionality and features provided by the proprietary data logger and fugitive emissions data collection software application program supplied with such systems or to another such program that conforms to the rigid and fixed data formats used by conventional systems and equipment.

In addition, conventional fugitive emissions monitoring system equipment have several physical design constraints that significantly limit user efficiency when operating such equipment during monitoring operations in the field.

In particular, some conventional sample probes utilized in such vapor analysis systems include a one-dimensional visual display such as a liquid crystal display (LCD) integrated into the sampling probe to display to the user the current concentration levels of a compound in a vapor sample. As explained below, this presents difficulties when a user performs testing of a specific leak point by approaching the leak point and manually moving or positioning the probe within close proximity to the leak point such as a valve until the user views the highest concentration level of a detected compound that the vapor analyzer system indicates on the LCD flat panel display integrated into the sampling probe.

Conventional sampling probes also provide a selection of buttons that the user must utilize to input information into the vapor analyzer system to indicate to the system that the user desires the system to begin testing and recording concentration levels of the compound for the particular leak point being tested. However, due to the positioning and orientation of such conventional LCD displays and buttons, this testing operation requires two hands and the ergonomic design of conventional sampling probes can severely limit the effectiveness and ease-of-use of the sample probe during the collection of a vapor sample from a leak point. In some testing positions, such as a leak point high overhead or low to the ground, the user may be unable to determine at what time the gas vapor analyzer is detecting the highest concentration levels of the compound and thus the user may be unsure of when to instruct the vapor analyzer system to begin the testing or measurement operation and logging for that particular leak point.

Further still, the conventional design and placement of sampling probe buttons to activate the testing operation for a leak point make it difficult, if not impossible in many designs, for the user to activate the testing, measurement and data logging processing of the vapor analyzer due to difficulty in holding the probe and concurrently selecting the appropriate button of a variety of buttons integrated into conventional sampling probes for activation of the testing sequence.

Due to the combined effects of the fixed one dimensional display position within the conventional sampling probe and the current placement of conventional test activation buttons within conventional sampling probes, inaccuracies can result when performing fugitive emissions monitoring for leak points other than those that are easily reachable by the user of such conventional sampling probes.

Embodiments of the invention comprise several components that function together as a vapor analysis system to significantly overcome such deficiencies. Embodiments of the invention provide a vapor analysis system with improved capabilities for vapor analysis, ease of user operation for leak detection, measurement and data management for use in fugitive emissions monitoring or other vapor analysis applications. The vapor analysis system of the invention includes a system housing that includes a vapor analyzer capable of analyzing a vapor sample for detection of a compound that may be contained within the vapor sample. The system housing is portable and may be placed, for example, in a backpack or a person may wear it as an attachment to a belt so as to allow the person to move freely in the field during monitoring operations. A controller is coupled to the vapor analyzer and is programmed with a control program to produce an indicator signal indicative of a relative concentration of the compound detected by the vapor analyzer within the vapor sample. The system includes a sample probe including a housing having or defining a vapor channel through which a vapor sample is directed. A vapor cable couples the vapor channel to the vapor analyzer to allow collection and channeling of the vapor sample to the vapor analyzer for analysis and detection of a compound that may be contained within the vapor sample. A multi-dimensional user indicator is disposed on the housing of the sample probe, preferably on or along the periphery of its housing. The multi-dimensional user indicator is in communication with the controller to receive and operate in response to the indicator signal to indicate the relative concentration of the compound detected within the vapor sample for presentation via a multi-directional stimulus to a user of the vapor analysis system. The sample probe further comprises a user actuator coupled via a data communications channel to the controller to provide a user enter signal to the controller based on operation of the user actuator by a user of the vapor analysis system in order to control operation of a control program operating within the controller.

Certain embodiments of the system also include a handheld data entry device such as a keypad that is in communication with the controller in the system housing. The keypad provides additional unique capabilities that further enhance ease-of-use and system operation.

In operation, the control program causes the controller to operate the vapor analyzer in a monitoring or survey mode to continually collect and monitor the vapor sample for detection of one or more compounds that may be contained within the vapor sample. The control program can also cause the controller to modulate the indicator signal to control an operation of the user indicator, such as a light or speaker on or in the sample probe. Modulation is relative to the concentration of the compound detected by the vapor analyzer within the vapor sample such that a detected increase in concentration of the compound may for example, cause the controller to increase modulation of the indicator signal sent to the user indicator. The control program can also cause the controller to provide a predetermined threshold indicator signal modulation pattern when the vapor analyzer detects a threshold concentration of the compound that exceeds a predetermined value. Thus the user of the sample probe can, while holding the probe in almost any position, determine (e.g., visually, by simply viewing the multi-dimensional user indicator, or audibly if the user indicator produces sound) that the vapor analyzer has detected the threshold concentration of the compound. The user indicator may flash or beep according to a predetermined threshold indicator signal modulation pattern, so the user can quickly identify leaking equipment in the vicinity of the leak point. There may be a minimum threshold level where the system does not increase the modulation of the indicator signal if a detected vapor concentration is below a specified value.

During the survey mode, the control program can receive a first user enter signal corresponding to a first activation of the user actuator by the user of the vapor analysis system. The user actuator may be, for example, a button or trigger on the housing of the sample probe that can be operated by the same hand that holds the sample probe. In response to the first user enter signal, the control program enters a testing or sampling mode to begin recording, for a predetermined time period, the concentration of the compound that may be contained within the vapor sample testing. During the sampling mode, the control program can provide a testing indicator concentration signal to the user indicator to modulate the user indicator in a testing pattern to provide a visual or audible stimulus to the user to indicate that the vapor analysis system is operating in sampling mode for a predetermined test time period. At the end of the predetermined testing time period, the control program enters a sampling complete mode and provides a testing complete indicator signal modulation pattern to modulate the user indicator on the sample probe to indicate to the user that the sampling mode is complete.

In the sampling complete mode, the control program receives a second user enter signal corresponding to a second activation of the user actuator by the user of the vapor analysis system. In response to the second user enter signal, the control program causes the controller to save the recorded concentration of the compound associated with the vapor sample in a route entry record of a route entry database maintained in a memory coupled to the controller. The route entry record corresponds to the leak point at which the user operated the sample probe to collect the vapor sample. After saving the compound concentration value, the control program re-enters the survey mode to begin collecting a vapor sample again for the next leak point.

In addition, a vapor analysis system configured according to embodiments of the invention can operate in a reprogramming or upload mode to allow an administrator (i.e., a person responsible for maintaining the device) to reprogram or reload the control program that operates within the controller to accommodate additional or different software functions, route entry data formats, database fields, pick lists of menu items (to be explained) and different screen layouts as may be required or desired for particular vapor analysis or fugitive emissions monitoring activities. As an example, the administrator may require that route list information and particular route entry field formats or layouts of route list entries be modifiable to allow the vapor analysis system of this invention to interoperate with a variety of different third party proprietary and/or nonproprietary software applications that operate on stand-alone computer systems that can interface to the vapor analysis system of this invention. Accordingly, the vapor analysis system of embodiments of the invention supports user-defined and highly customizable record formats for the storage of vapor analysis data produced during monitoring operations.

Further still, the administrator is able to define custom menus called pick lists for specific leak points that provide the ability to define a list of customizable user choices that a user (i.e., a person using the device in the field) can interact with and select when editing route entry data using the system of this invention. For example, the software control program can be configured to allow the user to enter, from a selection of user defined choices, a selection of a leak source and particular repair method used to fix the leak in the event the system detects an excessive concentration level. The operator can design custom pick lists for presentation and collection of leak point specific data for each leak point. As another example, if a leak point is a valve, an operator might define a pick list for this leak point that allows the user to indicate, from a choice of pick list menu selections, what specific part of the valve was leaking or what specific valve part the user attempted to fix when a leak was detected. In this manner, embodiments of the invention provide a route list database with user definable fields for presentation and collection of user-defined data.

Other embodiments of the invention include methods for operating a sample probe and vapor analysis system to perform the various processing operations noted above and disclosed herein as embodiments of the invention. Still other arrangements of embodiments of the invention that are disclosed herein include software programs to perform the method embodiment steps and operations summarized above and disclosed in detail below. As an example, a control program application that operates as a software process in a controller in a vapor analysis system as explained herein is considered an embodiment of the invention. More particularly, a computer program product is disclosed which has a computer-readable medium including computer program logic encoded thereon that, when executed on at least one controller with a vapor analysis system, causes the controller to perform the operations (e.g., the methods and processing steps) indicated herein. Such a computer program product containing just the software for the control program and/or a route entry database containing the user defined fields, such as a pick list, is considered an embodiment of the invention. Such embodiments of the invention are typically embodied as software, logic instructions, code and/or other data (e.g., data structures) arranged or encoded on a computer readable medium such as an optical medium (e.g., CD-ROM), floppy or hard disk or other a medium such as firmware or microcode in one or more ROM, RAM, PROM, or flash chips or as an Application Specific Integrated Circuit (ASIC). These software or firmware or other such configurations can be installed into a vapor analysis system to cause such a device to perform the techniques explained herein as embodiments of the invention.

Other embodiments of the invention comprise just the sample probe. One such embodiment comprises a housing having or defining therein a vapor channel through which a vapor sample can be collected for distribution to a vapor analyzer. This sample probe also includes a multi-dimensional user indicator, such as an indicator disposed on the housing. The user indicator is capable of receiving and operating in response to the indicator signal to indicate a relative concentration of a compound detected by a vapor analyzer in the vapor sample for presentation via a multi-directional stimulus to a user of the vapor analysis system. In one embodiment, when activated, the user indicator produces a multi-directional signal from opposite sides of the sample probe that is visible by the user of the sample probe from opposing positions relative to a central axis of the sample probe housing. This allows a user holding the sample probe to view the concentration level or other indicator signals from many different positions or orientations of the sample probe. The probe preferably includes a single user actuator such as a button or trigger which a user can operate using the same hand with which he or she is holding the sample probe. This allows one handed operation. Other embodiments of the sample probe include various combination of other features, as explained herein, such as filters and a vapor cable detachable interface.

BRIEF DESCRIPTION OF THE DRAWINGS

The foregoing and other objects, features and advantages of the invention will be apparent from the following more particular description of embodiments of the invention, as illustrated in the accompanying drawings and figures in which like reference characters refer to the same parts throughout the different views. The drawings are not necessarily to scale, with emphasis instead being placed upon illustrating the embodiments, principles and concepts of the invention.

DETAILED DESCRIPTION OF THE INVENTION

Figure 1:
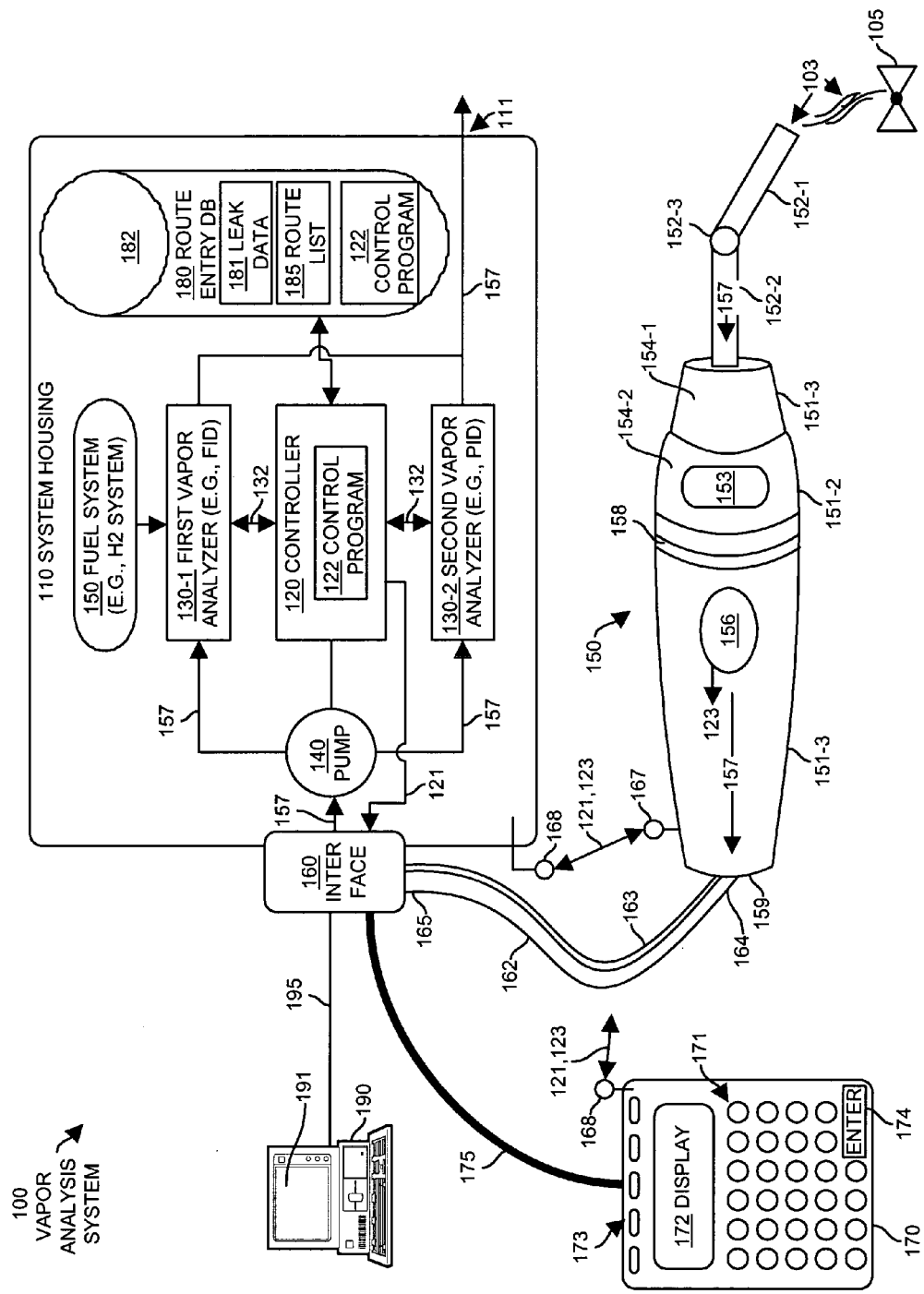
FIG. 1 illustrates a vapor analysis system configured in accordance with one embodiment of the invention.

FIG. 1 illustrates a vapor analysis system 100 configured according to one example embodiment of the invention. The example vapor analysis system 100 includes a sample probe 150 and a keypad 170 coupled via an interface 160 to a system housing 110. The system housing is portable and may be placed, for example, in a backpack or a person may wear it as an attachment to a belt so as to allow the person to move freely in the field during monitoring operations. The backpack can include a belt portion containing a holster, clip, snap or other attachment mechanism for the keypad 170 and the probed 150 for holding those items when note in use. A stationary computer system 190 operating a vapor analysis software management program 191 couples via a data communications link 195 to the interface 160 of the system housing 110. Generally, the stationary computer system 190 is not considered part of the vapor analysis system 100 during field operation of the system housing 110, the keypad 170 and the sample probe 150.

The system housing 110 includes a controller 120 such as a microprocessor, application-specific integrated circuit (ASIC), field programmable gate array (FPGA), programmable read-only memory, firmware, circuitry or other electronic and/or computerized hardware that operates (e.g., executes) a control program (e.g., a software process) 122 to control the general operation of the vapor analysis system 100 as will be explained herein. The control program 122 can control operation of one or more vapor analyzers 130 (two in this example, a first and second vapor analyzer 130-1 and 130-2) that may be vapor detectors. Each vapor analyzer 130-1 and 130-2 is capable of detecting the presence or existence of certain levels or concentrations of one or more compounds such as hydrocarbons that may exist within a vapor sample 103 that is collected from a leak point 105 and provided to the vapor analyzers 130 by a pump mechanism 140. The pump mechanism 140 couples to the interface 160 and is also under control of the control program 122 operating within the controller 120.

A storage device 182 such as one or more disk or memory systems is coupled to the controller and is capable of storing data associated with the operation of the vapor analysis system 100. Such data can include the software instructions for the control program 122 (e.g., code stored in a programmable read-only memory) and a route entry database 180 (e.g., stored in a battery backed random access memory) that contains a route list 185 containing records or fields of data and information related to specific route entry leak points such as leak point 105. The storage device 182 can also store leak point concentration levels and user selected data as leak point data 181 collected during operation of the vapor analysis system 100. This information is generally referred to herein as leak point data 181. The storage device 182 is generally persistent storage that maintains data in the absence of electric power and may be removable from the system housing. It is to be understood that the storage device 182 can be a combination of different storage mechanisms, such as one or more read only memory systems (ROMs or PROMS), random access memory systems (RAMs), Flash and/or magnetic memory such as disk. Examples of the storage device 182 include removable persistent memory devices such as flash memory cards, removable magnetic storage mediums such as floppy or hard disks, and the like. Note the control program 122 is shown as contained in both the controller 120 during runtime and as code in the storage 182 (e.g., when the power is turned off).

The sample probe 150 in this example is a handheld device that defines and houses a continuous tubular vapor channel 157 or path through which a vapor or gas sample 103 can pass through or travel from a tip or input end 152-1 of the sample probe 150 to a rear or output end 159 of the sample probe 150. The sample probe 150 is coupled to the interface 160 of the system housing 110 via a vapor cable 162. The vapor cable 162 continues the vapor channel 157 to the interface 160 and allows passage or collection and channeling of the vapor sample 103 to the vapor analyzer(s) 130 for analysis and detection of one or more compounds that may be contained within the vapor sample 103. The vapor cable 162 thus defines a portion of the entire vapor channel 157 and includes a vapor cable input end 164 that couples to a probe output end 159 of the sample probe and a vapor cable output end 165 that couples to an vapor input of the interface 160 disposed on or within the system housing 110.

The vapor cable input end 164 and vapor cable output end 165 can each be coupled and decoupled, respectively, from the sample probe output end 159 and vapor input of the interface 160, such that a user can replace the vapor cable 162 in an event of contamination or damage. Within the system housing, the vapor channel 157 continues from the interface 160 of the system housing to the pump 140 which can direct a vapor sample 103 to either one or both of the vapor analyzers 130-1 and/or 130-2 for analysis. The vapor analyzers 130 then exhaust the vapor sample 103 through the vapor sample exhaust port(s) 111 of the system housing 110.

According to the general operation of the vapor analysis system, during a monitoring and sampling mode of the control program 122 operating in the controller 120, as will be further explained, the pump 140 under control of the control program 122 creates a gentle suction or vacuum from the tip 152 of the sample probe 150 through the sample probe 150 and the vapor cable 162 to draw-in or collect a continuous vapor sample 103, as from the ambient air that is present at the tip 152-1 of the sample probe 150 near the leak point 105. The pump 140 channels this vapor sample 103 to the vapor analyzers 130 for analysis of compounds that may be contained within the vapor sample using vapor detection techniques such as, for example, flame ionization or photo-ionization. The compounds that may be detected may be, for example, hydrocarbons or other chemicals emitted as fugitive emissions from equipment corresponding to the leak point 105. The leak point 105 may be, for example, at or near a valve, pipe, pipe fitting, flange, vent, chemical processing equipment, or similar object.

In the illustrated example vapor analysis system 100, the first vapor analyzer 130-1 is a flame ionization detector (FID) that receives fuel such as hydrogen from a fuel system 150. The second vapor analyzer 130-2 in the illustrated example in FIG. 1 is a photo-ionization detector. Technology associated with of each of such detectors on an individual basis is well known in the art. It is to be understood by those skilled in the art that the vapor analysis system 100 can include one or more of any type of vapor analyzer capable of detecting any type of compounds in any type of gas sample.

As the vapor analyzer(s) 130 perform the process of detecting compounds within vapor samples 103 as explained herein, the vapor analyzers 130 produce a detected compound concentration level 132 that is output as an analog or digital signal for receipt by the control program 122 operating in the controller 120. As will be explained in more detail, the control program 122 can determine, based on the compound concentration level(s) 132, when a vapor analyzer 130 has detected a threshold concentration of a particular compound in a vapor sample 103. In such instances, the control program 122 records such information as being associated with a particular route entry (i.e., for a particular leak point) within the leak data 181 corresponding to the route list 185 that the controller 120 maintains within the route entry database 180. In one implementation, each vapor sample concentration reading is recorded as leak data 181 and references a specific route entry in the route list 185.

Prior to discussion of specific details of processing and user control of the vapor analysis system 100, attention is directed to the example sample probe 150 and its associated components configured according to example embodiments of the invention. In the embodiment shown in FIG. 1, the sample probe 150 includes a housing 151 that includes a handheld housing member 151-1, a liquid substance filter housing member 151-2 and a particulate filter housing member 151-3. Generally, the housing members 151 define and house a portion of the vapor channel 157 through which the vapor sample 103 is collected.

Each of the housing members 151-1 through 151-3 is constructed of a rigid material such as plastic or metal (e.g., aluminum alloy) and is generally cylindrical in shape, or shaped as a tapered cylinder in this example. Each housing member 151-1 through 151-3 couples to each other in this example embodiment using a male and female thread coupling mechanism (not specifically shown in this example illustration) such that the particulate filter housing member 151-3 can be rotatably screwed or threaded into or onto (depending on placement of male and female threads on each respective housing member) the liquid substance filter housing member 151-2, which in turn can be rotatably screwed or threaded onto or into the handheld housing member 151-1. Alternatively, the housing members 151-1 through 151-3 may snapped or held together using any appropriate mechanism.

The sample probe 150 includes one or more substance filters 154-1 and 154-2 (two in this example) disposed within the vapor channel 157. Generally, a substance filter 154 is capable of filtering at least one substance such as a liquid, dirt, sand, dust, oil, grime or other debris from the vapor sample 103 and the vapor channel 157 as the vapor sample 103 is collected through the vapor channel 157. The substance filter(s) 154 are removable according to embodiments of the invention to allow for replacement and/or cleaning as may be required. A user may accomplish removal of a substance filter 154, for example, by unscrewing or unsnapping or otherwise disconnecting the appropriate housing member 151-3 and/or 151-2 for access to the filter(s) 154. The substance filters 154 are manufactured to an appropriate size in this embodiment so as to fit snugly within an inner diameter of the cylindrical housing members 151-2 and 151-3.

In this example embodiment of the invention, the substance filter 154-1 is a particulate filter trap to extract and contain particulate matter that may be contained within the vapor sample 103 as the vapor sample is collected. The particulate filter trap 154-1 may be constructed of a semi-porous material such as sintered metal, mesh, fiber, or another material capable of trapping small particles and debris that may be drawn into the vapor channel 157 during collection of the vapor sample 103 while allowing the vapor sample 103 to pass through the substance filter 154-1.

The substance filter 154-2 in this example embodiment is a liquid (e.g., water) filter trap that can extract and contain liquid from the vapor channel 157 as a user uses the probe 150 to collect a vapor sample 103. The liquid filter trap 154-2 can extract and contain or trap liquid such as water, petroleum, oil or other liquids that may be inadvertently drawn into the vapor channel 157 due either to the suction that the pump 140 provides during vapor sampling or due to the user inadvertently allowing liquid to enter the sampling probe tip section 152-1, for example, during vapor testing activities in which the sample probe is held overhead or touches a dripping object that accidentally allows liquid to flow or drip into the sample probe tip 152-1. The liquid filter trap 154-2 can include, for example, a filter membrane disposed within the liquid filter trap defined by the probe housing 151-2 in a position that is transverse to the flow of vapor through the vapor channel 157. The liquid filter trap 154-2 (i.e., the filter membrane in combination with a reservoir housing defining a liquid storage cavity within the housing 151-2) does not allow liquid to pass through the filter housing 151 in the direction of flow 157, but does allow vapor, gas and air to pass in this direction. A liquid filter trap housing 154-2 defines a reservoir via, for example, a plastic cylinder that can be inserted and maintained in place within the sample probe housing member 151-2 and that can hold an amount of liquid while still allowing vapor to pass through the vapor channel 157 in the sample probe 150. The liquid filter trap housing 154-2 can have perforations or other small openings on an end closest to the probe tip 152 to allow liquid to enter the housing 154-2, and can contain a filter membrane that seals a downstream end closest to the probe housing 151-3 such that liquid is trapped within the housing 154-2. The liquid filter membrane within the liquid filter trap 151-2 can be disposed to seal a downstream end of the direction of flow in the vapor channel, so as not to allow liquid (but to allow vapor) to continue passing in the vapor channel 157 beyond the probe housing member 151-2 towards the system housing 110. A membrane sealing the downstream end of the liquid filter housing 154-2 can be made of a woven or fibrous material and can be removable to be replaced if it becomes excessively dirty or clogged with debris over time.

In this example embodiment of the invention, the liquid substance filter housing member 151-2 thus defines a liquid filter trap containment section (i.e., the housing member 151-2 itself) to position and maintain the liquid filter trap 154-2 within the vapor channel 157 at a location after the particulate filter 154-1 in a path of vapor sample travel through the vapor channel 157 within the sample probe 150. Accordingly, the particulate filter trap 154-1 first traps any physical debris that may enter the vapor channel 157 and thereafter, the liquid substance filter trap 154-2 traps and contains a liquid within the vapor channel 157. Accordingly, after the vapor sample 103 passes through the particulate filter trap 154-1 and the liquid substance filter trap 154-2, the vapor sample 103 is substantially comprised of the vapor sample 103 only (and potentially a vaporous compound distributed or mixed in with the vapor sample 103) and does not contain substantial amounts of liquid or physical debris.

Preferably, the liquid substance filter trap 154-2 is constructed of a translucent material such as clear plastic, Lucite, Lexan, glass, or a similar material that forms a liquid reservoir. As illustrated in the example embodiment of the sample probe 150 in FIG. 1, the liquid filter trap containment section defined by the inner portion of the liquid substance filter housing member 151-2 defines or contains a liquid filter trap window 153 that allows a user of the vapor analysis system who is viewing the sample probe 150 (when assembled as shown in FIG. 1) to visually inspect the contents of the liquid filter trap 154-2 to determine if any liquid is contained within the liquid filter trap 154-2. In other words, the liquid substance filter housing member 151-2 of the sample probe 150 has one or more cavities or holes or openings defined in its sidewall that visibly expose to a user of the sample probe a portion of the outer side of the translucent liquid filter trap 154-2 reservoir. In this manner, as a user operates the sample probe 150 during collection of vapor samples, he or she may periodically visually inspect the liquid substance filter trap 154-2 by peering through the liquid filter trap window 153 into the liquid substance filter trap 154-2 to make a visual determination whether or not any liquid has been trapped therein.

If, for example, the user accidentally collects an amount of liquid such as some water (e.g., water droplets) when performing fugitive emissions testing during collection of vapor samples 103 from one or more sample leak point areas 105, as the liquid substance filter trap 154-2 traps and begins to collect this water, the user can quickly become aware that water is present within the vapor channel 157. Upon making this determination, the user can decouple (e.g., unscrew or unsnap) the liquid substance filter housing member 151-2 from the handheld housing member 151-1 and can remove the liquid substance filter trap 154-2 in order to dispose of any liquid contained therein. A user can accomplish liquid disposal, for example, by shaking the removed liquid filter trap 154-2 such that any liquid flows out of this trap. Thereafter, the user can replace the liquid substance filter trap 154-2 into the housing member 151-2 and can re-couple that housing member 151-2 to the handheld housing member 151-1. Upon removing the liquid substance filter trap 154-2, the user may also elect to inspect the particulate substance filter trap 154-1 at this time to determine if any debris is present in the particular substance filter trap 154-1. It is to be understood that while the example illustrated embodiment shows the liquid filter trap window 153 defined in the wall of the liquid substance filter housing member 151-2 and no participate filter trap window, an alternative embodiment of the invention provides that a particulate filter trap window be defined within the particulate filter trap housing member 151-3 in order to allow the user to inspect for the presence of any trapped debris collected by the particulate filter trap 154-1.

In yet another embodiment of the invention, the liquid substance filter housing member 151-2 and/or the particulate substance filter housing member 151-3 are constructed of a translucent material such as plastic, Lucite, Lexan, glass or equivalent material so as to allow a user to quickly visually inspect the contents of the liquid substance filter 154-2 and/or the particulate substance filter 154-1 for the presence of any liquid or trapped physical debris.

In this example embodiment of the invention, the sample probe 150 includes a flexible sample probe tip 152 including tip sections 152-1, 152-2, 152-3 that form the input end of the vapor channel 157. The sample probe tip section 152-2 is coupled to an input end of the vapor channel 157 within the sample probe housing. The sample probe tip section 152-3 forms a hinged joint between tip sections 152-1 and 152-2 thus forming a flexible sample probe tip 152 that a user can manually position along a sample axis (i.e., of tip section 152-1) that is different from a central axis of the vapor channel 157 within the sample probe (i.e., of tip section 152-2 that extends into and is coupled to the sample probe housing 151). In this example embodiment, the sample probe tip section 152-3 is illustrated as a hinged joint and allows the internal passage of the vapor sample 103 through tip sections 152-1 and 152-2. In an alternative embodiment of the invention, the sample probe tip 152 or a portion thereof may be constructed of a flexible conduit material that a user of the sample probe 150 may bend or form into a desired position at an angle relative to the sample probe housing 151 that provides optimal positioning for collecting the vapor sample 103 from a particular leak point 105. Since embodiments of the invention provide a flexible sample probe tip 152, difficult or hard to reach leak point sampling areas 105, such as obstructed valves or pipe flanges or leak points that are high or low relative the user are easy to access for sample collection.

The sample probe 150 configured in accordance with embodiments of the invention further includes a multi-dimensional user indicator 158 that is in communication with the controller 120 via a data communications channel 163 to receive and operate in response to an indicator signal 121 to indicate, for example, the relative concentration of the compound detected within the vapor sample for presentation via a multi-directional stimulus such as light or sound or vibration to a user of the vapor analysis system. By multi-dimensional, it is meant that in embodiments of this invention, the user indicator 158 is non-planar (as opposed to a flat panel display in conventional systems) and its signal can be readily sensed regardless of orientation of the probe. For example, the user indicator 158 may be disposed around a circumference of a central axis of the housing 151 defined by the vapor channel 157. The user indicator 158 thus produces a multi-directional signal from opposite sides of the sample probe 150 that may be perceived, (seen heard, felt) or audible by a user of the sample probe 150 from essentially any position around the circumference of the probe 150. In other configurations, the controller 120 sends a concentration signal 121 to a processor in the keypad 170 which operates processing to control the modulation signal sent through the interface cable 163 to control the user indicator 158. That is, in one design of the system 100, the controller 120 sends the modulation signal 121 to a processor in the keypad 170 that interprets this concentration level as a signal and produces a corresponding modulation signal that is transferred via keypad connection 175, through the interface 160, and through the sample probe interface cable 163 to control electronics within the sample probe 150 to modulate the user indicator 158. In other configurations, the data communications channel 163 can be coupled directly to the keypad device 170 to receive the modulation signal that controls the user indicator 158. It is to be understood that the particular configuration and placement of the processing circuitry as illustrated in FIG. 1 to control the user indicator 158 is not intended to be limited to embodiments of the invention. In one embodiment, the user indicator 158 is a light pipe disposed around the circumference of the sample probe housing 151. The light pipe user indicator 158 is constructed of a semi-transparent material such as shaded semi-transparent clear or colored (e.g., red or orange) plastic, glass or an equivalent material and is disposed or embedded as a strip or bead around the circumference of the handheld housing member 151-1. One or more light emitting diodes (LEDs), light bulb(s), filaments or other illumination mechanism(s) operable within the handheld housing member 151-1 provide backlit illumination for the light pipe according to different modulation flashing patterns, as will be explained. Upon illumination, the light pipe user indicator 158 disperses light produced from the light source throughout itself in a glowing manner in order to illuminate the user indicator 158 in multiple dimensions or positions around the entire circumference of the housing member 151-1. In this manner, the illumination is visible from multiple directions as the user holds the sample probe 150 due to the multi-dimensionality of the user indicator 158 and its positioning around the sample probe housing 151.

It is to be understood that the particular positioning and construction of the user indicator 158 in the embodiment illustrated in FIG. 1 is shown by way of example only and that many other configurations are possible. As an example, the user indicator 158 could be a series of two or more LEDs or other lights (e.g., small light bulbs) disposed on, in or around the housing 151 of the sample probe 150. The user indicator 158 could also be disposed on, in, or around the probe tip 152. In another alternative configuration, a portion of the sample probe housing 151 may itself be translucent and the user indicator may be an internal light source within the housing that emits light from the illuminated housing 151 in many opposing directions around the periphery of the sample probe housing 151. To this end, embodiments of the invention generally provide a user indicator 158 that produces a multidimensional user stimulus that is perceptible (e.g., visible) by a user regardless of orientation of the sample probe 150. As will be explained, the control program 122 can modulate a concentration signal 121 that controls the user indicator 158 for example, to make the illuminated user indicator 158 flash or vary in brightness, intensity or other type of level to indicate to the user certain operational modes of the control program 122 and to indicate, for example, a concentration level 132 of the compound that a vapor analyzer(s) 130 detects in the vapor sample 103.

While the illustrated user indicator 158 in the foregoing examples is an illumination mechanism such as a light or light pipe, other multidimensional user indicators could be substituted for the light or can be provided in addition to a light source user indicator 158. As an example, according to another embodiment of the invention, the user indicator is a sound source such as a speaker or audible transducer mounted on or within the sample probe 150 or within an earpiece that an operator wears. In the case of an earpiece, a modulation signal provided to the earpiece may be sent using a wireless transmission signal from either the keypad 170, the sample probe 150 or from a transceiver mounted in the housing 110. The audible user indicator can produce sound such as a beeping or tone pattern or other tone based upon the indicator signal 121 that it receives from the control program 122 over the data communications channel 163. The pitch, tone or beeping frequency of such an audible user indicator can convey to a user the operative state of the control program 122 and the relative concentration level 132 of a compound existing within the vapor sample 103. It is to be understood that a sample probe 150 configured according to embodiments of the invention can include one, or more than one, type of user indicator such as a light pipe 158 in addition to a speaker or vibration mechanism mounted elsewhere within the housing 151 of the sample probe 150. If the user indicator 158 is a vibration mechanism, the controller 120 can modulate the signal 121 to control the amount of vibration felt by the user.

In this example, the data communications channel 163 is one or more physical signaling wires or conductors such as a data communications cable, data bus, or other signaling means that is disposed within or coupled alongside the vapor cable 162 that couples the sample probe 150 to the system housing 110 via the interface 160. In an alternative embodiment of the invention, the data communications channel 163 may be a wireless communications signaling channel enabling transmission of data between wireless transceiver units 167 and 168 that include antennas located within the housing of sample probe 150 and within the system housing 110 or within the keypad 170. Those skilled in the art will understand that there may be many different types of wireless communications protocols suitable for use in this manner to enable communications between the sample probe 150 and the system housing 110 that operates the controller 120. In addition, as noted above, in another configuration, the modulation signal 121 is a concentration level or signal sent from the controller 120 to a processor in the keypad 170 which the interprets this signal 121 to produce a modulation signal that is then sent to electronics in the sample probe 150 to control modulation of the user indicator 158. In such cases, the data communications cable 163 can couple to the interface 160 and receive the signal from the keypad 170 via the path of cable 175, through the interface 160, and through the data communications cable 163, or alternatively the data communications cable can couple to the keypad 170.

As noted above, the user indicator 158 is coupled to the data communications channel 163 to receive and operate in response to the indicator signal 121 (from either the controller 120, or from the keypad 170 that receives the signal 121) to indicate such data as the relative concentration of a compound(s) detected by the vapor analyzer(s) 130 within the vapor sample 103 for presentation via the multi-directional light, sound, or vibration stimulus to a user of the vapor analysis system 100. The control program 122 can modulate the indicator signal 121 for other purposes as well, such as to indicate to the user when the vapor analyzer has detected threshold levels of concentrations of a compound, when testing begins and ends, when the user is able to save the test results into a route entry in the route list 185, and for signaling error conditions to the user.

Prior to a detailed discussion of specific operating modes and patterns (e.g., flashing of the light or beeping of a speaker) of the user indicator 158, another feature referred to as a user actuator 156 provided on or within a sample probe 150 configured according to embodiment of the invention will now be discussed. The combination of operations of the user actuator 156 and the control program 122 in controller 120 and activation or operation of the user indicator 158 will be provided in detail hereafter according to different operating modes of the vapor analysis system 100.

According to embodiments of the invention, the sample probe 150 further includes a user actuator 156. Depending upon the specific configuration, the user actuator 156 may be, for example, a button, trigger, wheel, switch or other user operable signaling or switching mechanism that is mounted on or within the housing 151 (preferably on or within the handheld housing member 151-1) and is coupled via the data communications channel 163 to allow communications with the controller 120. When operated by the user, the user actuator 156 provides a user enter signal 123 to the controller 120 in order to control operation of the control program 122 operating within the controller 120. As noted above, it is to be understood that the control program 122 can operate either within the system housing 110 as shown in FIG. 1 or within the keypad 170 (on a processor contained therein). As will be explained in more detail shortly, a user holding the sample probe 150 can actuate a button serving as the user actuator 156, such as by depressing the button 156 with a thumb or forefinger, which causes the user actuator 156 to generate a user enter signal 123 that is transmitted over the data communications channel 163 for receipt by the control program 122 operating within the controller 120. A user of the sample probe 150 might decide to provide such a user enter signal 123 during certain operational modes of the control program 122, such as when operating in a survey mode to cause the control program to begin performing fugitive emissions testing of vapor samples at a leak point 105 for detection of certain compounds. Specific uses of both the user indicator 158 in conjunction with operation of the user actuator 156 will be explained in detail shortly with respect to a description of the functionality and processing operations of operating modes of the control program 122 in the vapor analysis system 100.

Also as illustrated in FIG. 1, a vapor analysis system 100 configured according to certain embodiments of the invention includes a data entry device 170 such as a keypad that is capable of communicating with the controller 120 in the system housing a data entry communications channel 175. The data communications channel 175 can either be a physical or wireless communications link between the keypad 170 and the interface 160 of the system housing 110 in order to allow bi-directional communications between the keypad 170 and the control program 122 operating in the controller 120. In this example embodiment, the keypad 170 includes a set of alphanumeric data entry buttons or keys 171, a display 172 and a set of special function keys 173. One of the data entry keys is designated as a "return" or "enter" key 174.

During operation of the control program 122, the control program 122 is able to output information over the data entry communications channel 175 for display on the display 172 of the keypad 170 for presentation to a user of the vapor analysis system 100. In addition, the user is able to input information to control program 122 by depressing sequences of data entry keys 171 and by using the user enter key 174. In addition, the special function keys 173 enable the user to quickly select common or frequently used functions of the vapor analysis system 100.

As an example, in one embodiment of the invention a special function key 173 permits viewing of information within the route entry database 185 maintained in storage 182 in order to confirm or review collected concentration data or other information such as concentration data, notes, comments, etc. about a leak point associated with a specific route entry. Another function key 173 in another embodiment of the invention provides access to multiple analyzer functions of the vapor analyzer(s) 130 and controller 120 to activate a flame ionization detector vapor analyzer 130-1 and cause the control program to enter the survey mode to begin testing vapor samples for traces of a compound. By providing abbreviated functionality to the user by allowing the user to select a specific special function key 173, embodiments of the invention significantly reduce the need or requirement of the user to directly and frequently interact with the system housing 110 in order to operate vapor analyzer 130 functionality. Instead, the user can operate such functions remotely from the data entry device keypad 170.

In addition, since the keypad data entry device 170 is a physically separate device from the sample probe 150 according to embodiments of the invention, during typical operation of the vapor analysis system 100, such as when performing fugitive emissions testing of many leak points in succession, the user may only periodically require interaction with the keypad 170 and can perform typical or standard operations using the user actuator 156 on the sample probe in conjunction with viewing modulation patterns of the user indicator 158 (e.g., the light flashing or sound beeping according to a predetermined pattern) in order to determine the current operation or state of the control program 122 for progression through a series of testing operations associated with route entries in the route list 185 defining a series of leak points 105 to be tested.

In particular, in one embodiment of the invention, the user actuator 156 according to one embodiment of the invention mimics or duplicates operation of the enter key 174 on the data entry device 170. Accordingly, if the user holding the sample probe 150 depresses the user actuator 156, the control program 122 receives a user enter signal 123 in the same manner (i.e., the same signal) as if the user had depressed the enter key 174 on the keypad 170. Thus the user can either depress the user actuator 156 on the sample probe 150 or can press the enter key 174 on the keypad 170 and the same user enter signal 123 is received by the control program 122 in both instances.

As will be explained, this feature of embodiments of the invention allows a user to not have to constantly refer to and interact with the keypad 170 to control typical and often repetitive operational functionality of the vapor analysis system 100. As an example, since the probe 150 includes a user actuator 156 that can produce the user enter signal 123, during routine operation of traveling from one leak point 105 associated with one route entry in the route list 185 to another leak point 105 of the next entry (at another location in the field), and when performing testing of vapor samples 103 for each of these leak point sample areas 105, the user can easily perform such testing by interacting only with the sample probe 150 via activation of the user actuator 156 and by viewing the modulation patterns of the user indicator 158 according to the techniques explained herein. This allows the user to perform one-handed operation of the vapor analysis system 100 when testing leak points in route list, as opposed to conventional sample probe and keypad combinations that require two-handed operation and that often require the user to interact with a keypad having many different keys that can confuse the user and overly complicate the testing procedure.

Further still, since embodiments of this invention separate the keypad 170 from the sample probe 150, the sample probe remains lightweight and is easily handled by a user for testing many hundreds of sample areas 105 of leak points without significant hand or arm fatigue. Some conventional systems require the user to support, with one hand, both keypad and the sample probe mechanisms and require two-handed operation and frequent interaction with a keypad containing a complex array of small keys. Since the sample probe 150 of embodiments of this invention is separate from the keypad 170, the probe has a significantly smaller form factor and thus leak points that may be difficult to reach, such as in small spaces or tight quarters, are easier to test. In addition, the user actuator 156 and user indicator 158 of the probe permit fast, simple testing of leak points.

For operations that require interaction with the keypad 170, generally, and also as will be explained in more detail shortly, the display 172 of the keypad 170 allows the control program 122 to provide a variety of data, information fields, and menus to the user during operation of the vapor analysis system 100 and allows the user to provide user definable and selectable information and data as input to the control program 122. In one embodiment of the invention, the display 172 supports a concurrent display of many rows and columns of alphanumeric and or graphical information and menus for presentation to the user of the vapor analysis system 100 to allow the user to view large amounts of detail, if required, regarding operation of the control program 122. As an example, the display 172 may support the concurrent display of eight rows by twenty columns of alphanumeric character information. It is to be understood that other screen resolutions can be used as well.

Next there will be explained the several unique processing capabilities provided by the control program 122 operating within the controller 120.

Figure 2:
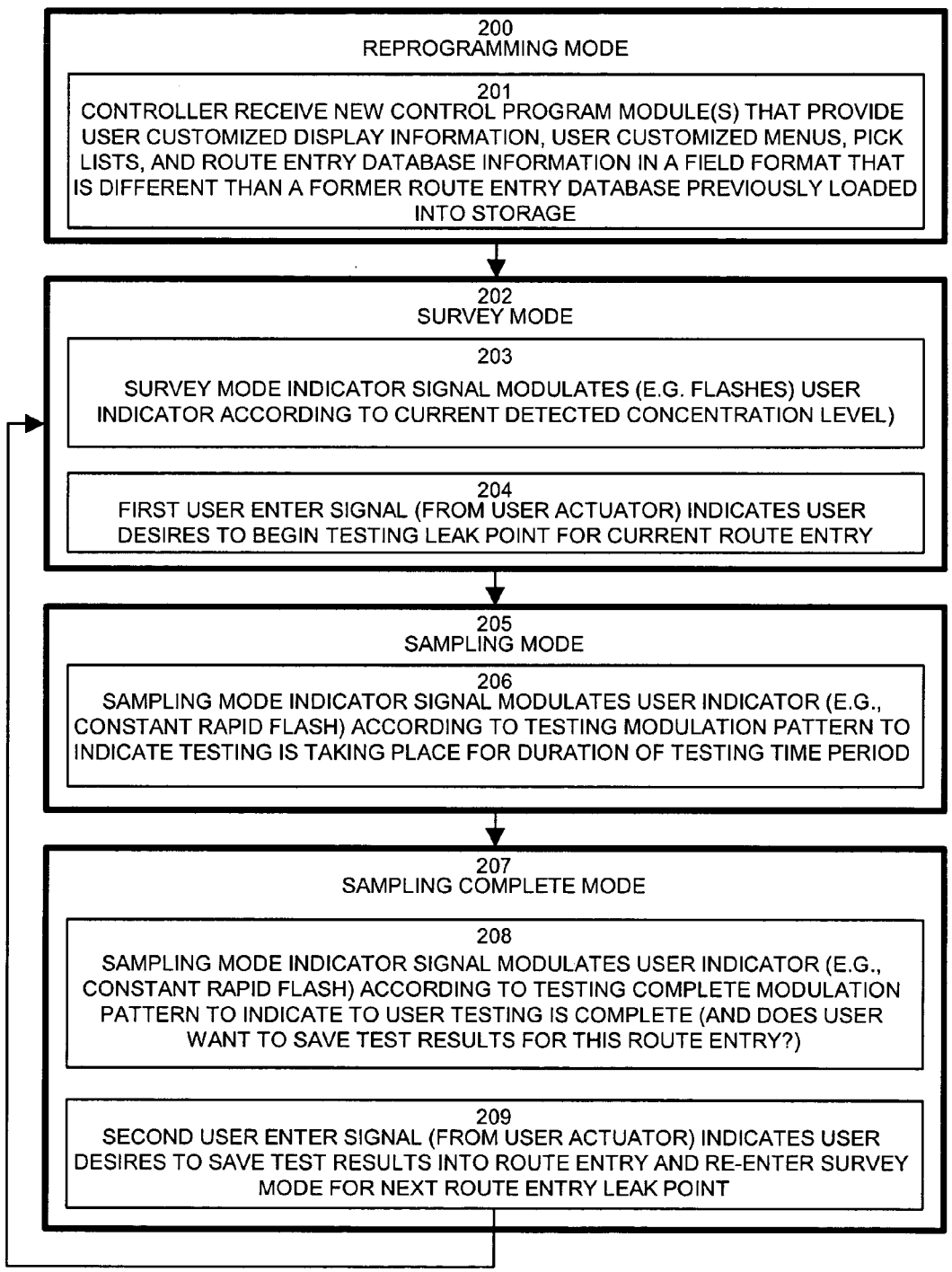
FIG. 2 is a flow chart showing operational modes of a control program operating in a controller in a vapor analysis system configured according to one embodiment of the invention.

FIG. 2 illustrates example operating modes of the control program 122 operating within the controller 120 in accordance with one example embodiment of the invention. In this particular example, the control program 122 is configured with logic instructions (e.g., software code and/or data) to support operation in a re-programming mode (step 200), a survey mode (step 202), a sampling mode (step 205) and a sampling complete mode (207). Each of the operating modes shown in FIG. 2 will be discussed briefly with respect to this figure. Specific operational details of the monitoring, testing and testing complete operating modes (details of steps 202, 205 and 207) will also be further explained with reference to separate respective flow charts presented in FIGS. 3 through 5.

In step 200 in FIG. 2, the control program operates in a reprogramming mode that enables the vapor analysis system 100 to be reconfigured to accommodate different route entry database record formats for the route list 185 to allow a user to configure the route entry database 180 to match a data record format in use by the fugitive emissions vapor analysis software management program 191 that operates within the stationary computer system 190. In particular, in the reprogramming mode the control program 122 can download, from the stationary computer system 190, a user-customized route entry database 180 such as a text file that includes a route entry record definition of what fields and field formats exist in the route list 185. Each route entry record in the route list 185 defines route entry leak point data and information associated with a respective leak point sample area 105. The entire route list 185 thus defines a list of route entry records that collectively form the route entry database 180 and each record corresponds to a respective leak point 105 for which the user can use the vapor analysis system 100 to sample or check for leaks during his or her route in the field (e.g., within a facility when performing fugitive emissions testing). Generally, this list of leak points is referred to as the route list 185, and the route entry database 180 is the collection of route list entries and all related route entry field data for each route entry record.

As one example of a data format of a single route entry record within the route list 185, each route entry (i.e., each route entry record in the route entry database 180) can contain the following data fields:

A database key field for this route entry

A leak point identification field, such as a number, bar code pattern, or tag identity associated with a specific leak point 105.

A maximum allowed leak concentration field of a compound for this leak point

A minimum concentration level field to cause activation of the user indicator 158 to show that the vapor analyzer is detecting a compound of interest (i.e., that the leak point is actually leaking as opposed to the vapor analyzer detecting an ambient level of the compound contained in normal vapor samples of air around a non-leaking leak point)

A response factor field (used in computing concentration levels of a compound)

The route entry number field (for display to a user)

A test time period identifying how long a vapor analyzer should perform concentration testing for this leak point when in the sampling mode. This time may vary depending upon the type of leak point being tested and the type of compound being tested.

A detected concentration level for this leak point (value is obtained and recorded during the sampling mode and saved during sampling complete mode)

A route entry string field providing a textual description of the leak point that is presented to the user to assist in locating the leak point A comment string field allowing the user to enter a text comment string concerning the leak point associated with this route entry (value obtained during user operation in field, if user elects to provide such information)

A pick list of menu items and associated operational modes for this leak point that defines a set of one or more user customized menus that the control program can present to the user during certain operational modes. Each pick list can indicate the operational mode during which the control program is to display the pick list (i.e., during operation of that mode). Two hypothetical examples of pick list menus that can be included in a route entry record uploaded with the route list 185 into the storage device 182 include:

1. A leak source pick list defining a selection of sources of a leaking compound for this leak point—displayed during sampling complete mode if the concentration level exceeds the minimum concentration level for this route entry record. As an example, a route entry record for a leak point associated with a valve installed in a pipe might have a leak source pick list defining user selectable choices to assist in specifically locating the leak, such as: 1: Valve handle; 2: Valve packing; 3: Valve body; 4: Valve inlet coupling; 5: Valve outlet coupling, and so forth.

2. A repair method pick list defining user selectable choices for methods that the user employs to attempt to fix a leaking leak point. This pick list is displayed by the control program if the user indicates, during sampling complete mode, that he or she desires to attempt to fix the leak point. Example choices might include: 1: Tightened valve nut; 2: Repacked valve packing; 3: Resealed valve coupling; 4: Shut off valve; and so forth.

A pick list selection field for each pick list capable of holding at least one user selected value from the pick list menu items.

Note that some record fields of the above route entry record format are pre-populated with data that the control program accesses and uses during testing (e.g., minimum concentration level), while other fields such as the highest detected concentration level store data that the control program or user provides or calculates when sampling and using the system 100 in the field. It is to be understood that any field can be defined as a pick list and can be used to define data that a user can select during operation to customize the route list for a particular use, such as for example, allowing the user to select a particular plant name, whether or not a leak point was difficult to monitor, and other such customized and user defined information.

In one embodiment, the vapor analysis system includes a leak point identification mechanism such as a global positioning system transceiver (not shown) e.g., on or within the sample probe capable of detecting a global position location value upon user activation of the user actuator 156 (FIG. 1). In response, the leak point identification mechanism provides a global position location value as the leak point identification value to the controller 120 for storage within the route entry associated with leak point from which the vapor sample is collected. In another alternative embodiment, the vapor analysis system 100 includes a radio frequency tag identification reading mechanism or a bar code scanner (not specifically shown in FIG. 1) capable of reading an tag identity of a leak point from a radio frequency tag or bar code tag positioned in proximity to the leak point. The leak point identification mechanism provides the tag identity as the leak point identification value to the controller 120 for storage within the route entry associated with the leak point from which the vapor sample is collected.

In the aforementioned example route entry record format, pick list menu entries are alphanumeric database fields of user-selectable (i.e., user pickable) menu items that allow a vapor analysis system administrator to custom design a route list for specific leak points. These custom designed menus allow a user to provide customized menu choices having predefined values that the control program can provide as a set of user selectable options during operational modes. As an example, the control program 122 can display a pick list of user-selectable menu items within the display 172 of the keypad 170 during operation in an operating mode associated with that pick list. Pick list values may be text or numeric strings that an administrator of the vapor analysis system defines in the route entry database records prior to being uploaded from the stationary computer system 190 to the vapor analysis system 100.

By way of example, using the above example pick list 1 defining specific leak locations for a valve leak point 105, if the control program 122 determines that the concentration level 123 for this leak point 105 exceeds the maximum concentration level field defined in the route entry record for this leak point 105, then the control program 122 in a sampling complete mode can display the pick list 1 (above) to allow the user to specifically identify what portion of the valve at the leak point 105 was leaking (e.g., the valve handle, packing, coupling to a pipe, and so forth). The user selection will correspond to the location around the valve at the leak point 105 at which the user positioned the sample probe tip 151-1 and observed the highest concentration level. The control program can save the user selected result in the pick list selection field so that when the route list 185 is downloaded back into the stationary computer system 190 for analysis of the field test results of leak points, this information can be further used to clarify certain details about leak points 105 that may have been leaking. This aspect of embodiments of the invention allows an operator of the stationary computer system 190 to develop customized pick lists for fields within a route entry. That way, when the operator in the field is performing the vapor analysis process explained herein, the operator can simply pick a predefined string of text as one of the choices from the pick list and it avoids problems with different operators using different terminology when trying to describe information related to a particular leak point.

In addition, in the reprogramming mode in step 200, the control program 122 can be upgraded such that software modules associated with the control program 122 can be replaced with newer software modules that accommodate additional operating features such as being able to use the new route list record formats defined in the route list 185.

As shown in sub-step 201 in FIG. 2, in the reprogramming mode the controller 120 can receive new control program modules 122 that provide and can access and use user customized display information and user customized menus (e.g., pick lists) and user-defined information in route entry database 180 and route list 185 from a former route entry database 180 previously loaded into storage device 182. In other words, the processing of the controller 120 in step 201 allows the user to replace a current route entry database 180 in the storage device 182 with a new route list 185 having a different set of fields or values for data within the route list 185 and allows the user to update the control program 122 to be able to work with the new route entry record format. The control program may be, for example, software code and/or data that can be erased and reloaded into disk storage in the storage device 182, or that the controller 120 can reload into firmware such as an electrically erasable programmable read-only memory (EEPROM), or a similar device. Such replaceable information may be stored in random access memory backed up by a battery and the route database information can contain changeable data. By being able to replace and/or update both the control program 122 and/or the route entry database information 180, embodiments of the invention allow full reprogramming of the controller 120 to accommodate different database fields formats as well as different user interface information presented to the user during control program operation modes.

In Step 202, the control program 122 generally operates in a survey mode to cause the controller 120 to operate the vapor analyzers 130 to continually collect and monitor vapor samples 103 for detection of compound(s) that may exist within the vapor sample 103.

As part of the survey mode operation, as shown in sub-step 203, the control program 102 provides a monitor mode indicator signal 121 that modulates (e.g., flashes or beeps) the user indicator 158 on the sample probe 150 according to the current detected concentration level 132 of a compound within the vapor sample 103. In other words, during control program operation in the survey mode, the control program 122 operates the user indicator 158 by modulating the survey mode indicator signal 121 that causes the user indicator 158 to flash or beep at a rate that reflects, to the user, the relative concentration level 132 of the detected compound in the vapor samples 103.

In addition, during the survey mode, the control program 122 can provide a concentration exceeded survey mode concentration signal 121 such as an intermittent bright flash (e.g., once every three seconds) that provides a modulation pattern to indicate, for example, when the vapor analyzer 130 has detected a level or concentration of the compound for this leak point that has exceeded a maximum predefined threshold concentration level (e.g., as defined by the maximum concentration level in the example route entry record discussed above). This special concentration exceeded survey mode concentration signal 121 thus indicates to the user that the leak point is actually leaking some compound since the maximum level of the compound is typically set (i.e., by an administrator), for a leak point, above a level of the compound that may be present in ambient air surrounding a non-leaking leak point.

In addition, in sub-step 204 during survey mode, the control program 122 can detect a first user enter signal 123 from the user actuator 156 that indicates that the user at that moment desires to begin vapor analysis testing of the leak point 105 for the current route entry within the route list 185 of the route entry database 180. The control program 122 continuously attempts to detect activation of the user actuator 156 that causes the control program 122 to transition from the survey mode of step 202 to the sampling mode of step 205. According to a preferred operation of the vapor analysis system 100, a user operates the user actuator 156 to provide the first user enter signal 123 when that user perceives that the sample probe 150 is positioned at a sample area location 105 having the highest concentration of a compound, as indicated by the most rapid modulation (e.g., flashing or beeping) of the user indicator 158 while in the survey mode 202 (i.e., before the user operates the user actuator 156). Upon activation of the user actuator 156, the control program 122 transitions from the survey mode in step 202 to the sampling mode generally shown by step 205 in FIG. 2.

In the sampling mode in step 205, the vapor analyzer 130 continues to analyze the continuously collected vapor sample 103 for a predetermined time period or test interval, such as seven seconds (or another predetermined time period). During this sampling mode time period, the control program 122 can be continually receiving and temporarily recording (i.e., saving in memory in the controller) the concentration level 132 that represents the highest concentration of the compound contained within the vapor sample 103, as detected by the vapor analyzer 130 during the test time period or test interval.

In addition, as indicated in sub-step 206, when operating in the sampling mode, the control program 122 can provide a sampling mode indicator signal 121 to the user indicator 158 on the sample probe 150 in order to modulate the user indicator 158 according to a predetermined sampling mode modulation pattern to indicate to the user that the control program 122 is currently testing and recording the highest concentration level of the vapor sample 103 at the current leak point location 105 of the sample probe tip 152-1 for the duration of the testing time period (e.g., provides a rapid flash for seven seconds). Preferably, during sampling mode the user does not substantially move the sample probe tip 152-1 away from the location for the duration of the test time interval (e.g., seven seconds) as indicated by the test mode flashing pattern of the user indicator 158.

Note that in one alternative embodiment of the invention, the testing time period for this particular leak point associated with this route entry record in the route list 185 may be defined within the customized field format for this leak point 105. The test time period may be dependent upon the type of compound being tested for that leak point 105 or may be dependent upon the type of equipment associated with that leak point 105, such as a valve, flange or other equipment type. Such test time parameters can be defined in this alternative embodiment in the route entry record for the leak point such that the test time period for one leak point may be different than the test time period for another leak point that may be emitting a different compound.

In step 207, upon completion of the test time period (e.g., after seven seconds), the control program 122 enters a sampling complete mode. In the sampling complete mode, the control program 122 generally indicates to the user (e.g., via a flash or tone pattern unique to this mode) that the test time period has ended and that the test of this leak point is now done and the user is able to either save the record concentration level for that leak point 105 into the results field of the route entry associated with that leak point in the route entry database 180, or is able to operate the data entry device 170 to provide additional information concerning the testing procedure performed for that leak point 105.

More specifically, as shown in sub-step 208, in the sampling complete mode the control program 122 provides a sampling mode indicator signal 121 that modulates the user indicator 158 for example, in an alternating on-off flashing or beeping pattern, or according to another unique testing complete modulation pattern, to indicate to the user that testing is now complete for the vapor samples 103 collected at that test point 105. This testing complete modulation pattern presented to the user by the user indicator 158 allows the user to become aware that testing is complete for the vapor sample 103 and to determine if he or she wants to save the test results for this route entry in the route list 185 associated with this leak point 105.

In sub-step 209, in this example, the control program 122 receives a second user enter signal 123 from the user actuator 156 that indicates that the user of the sample probe 150 desires to save the temporarily recorded test results into a route entry of the route list 185 in the route entry database 180 and further desires to reenter or return to the survey mode in step 202 to begin testing the next route entry leak point. Note that the user can also interface with the keypad 170 at this point to review alternative options related to, for example, retesting the leak point, fixing the leak point, and the like. Further details of these alternative options will be explained later with respect to the detailed flow chart of processing steps in FIG. 5.

In this manner, the sequence of operating modes illustrated in FIG. 2 allows a user to initially program the vapor analysis system 100 with the control program 122 and a user customized route entry database 180 that contains user customized data and other information fields for a specific route list associated with a series of leak points 105. Thereafter, the user can operate the sample probe 150 to cycle through survey mode, sampling mode and sampling complete mode for each leak point 105 to continually test and save the test results and return to survey mode during that user's approach to the next leak point 105. In this manner, embodiments of the invention allow the user to operate the user actuator 156 on the sample probe 150 and view (or listen to or feel) various modulation patterns of the user indicator 158 on the probe in order to be able to identify the current operation of the control program 122 within the vapor analysis system 100. Using the features of embodiments of the invention, a user does not need to routinely interact with the data entry keypad device 170 on a leak point by leak point or other routine basis as the user tests one leak point after another.

Note that in one embodiment, the control program 122 itself is not changed during the reprogramming mode, but rather, the route entry database information 180 is modified to reflect changes to data associated with leak points, such as providing new pick list menu choices, minimum or maximum concentration levels, etc. In other embodiments, the control program 122 itself can be reloaded so that as new features are developed or optimizations to control program operation are created, they can be integrated into the system 100. Furthermore, it is to be understood that in reprogramming mode, the user couples the system housing 110 to the stationary computer 190. This can be done to allow the stationary computer 190 to retrieve or download the leak data 181 containing sampled concentration levels for each leak point, as well as user selected pick list menu choices, comments and other information collecting during the field use of the system. That is, reprogramming mode does not have to include reconfiguring the control program 122 and/or the route list 185, but can simply include obtaining any or all collected data from use of the device in the field to perform fugitive emissions data collection and monitoring.

Now that a high level overview of the various operating modes performed by the control program 122 has been presented, specific operating mode details with respect to the survey mode, the sampling mode and the sampling complete mode will be explained with reference to the flow chart of processing steps associated with these various operating modes shown in FIGS. 3 through 6.

Figure 3:
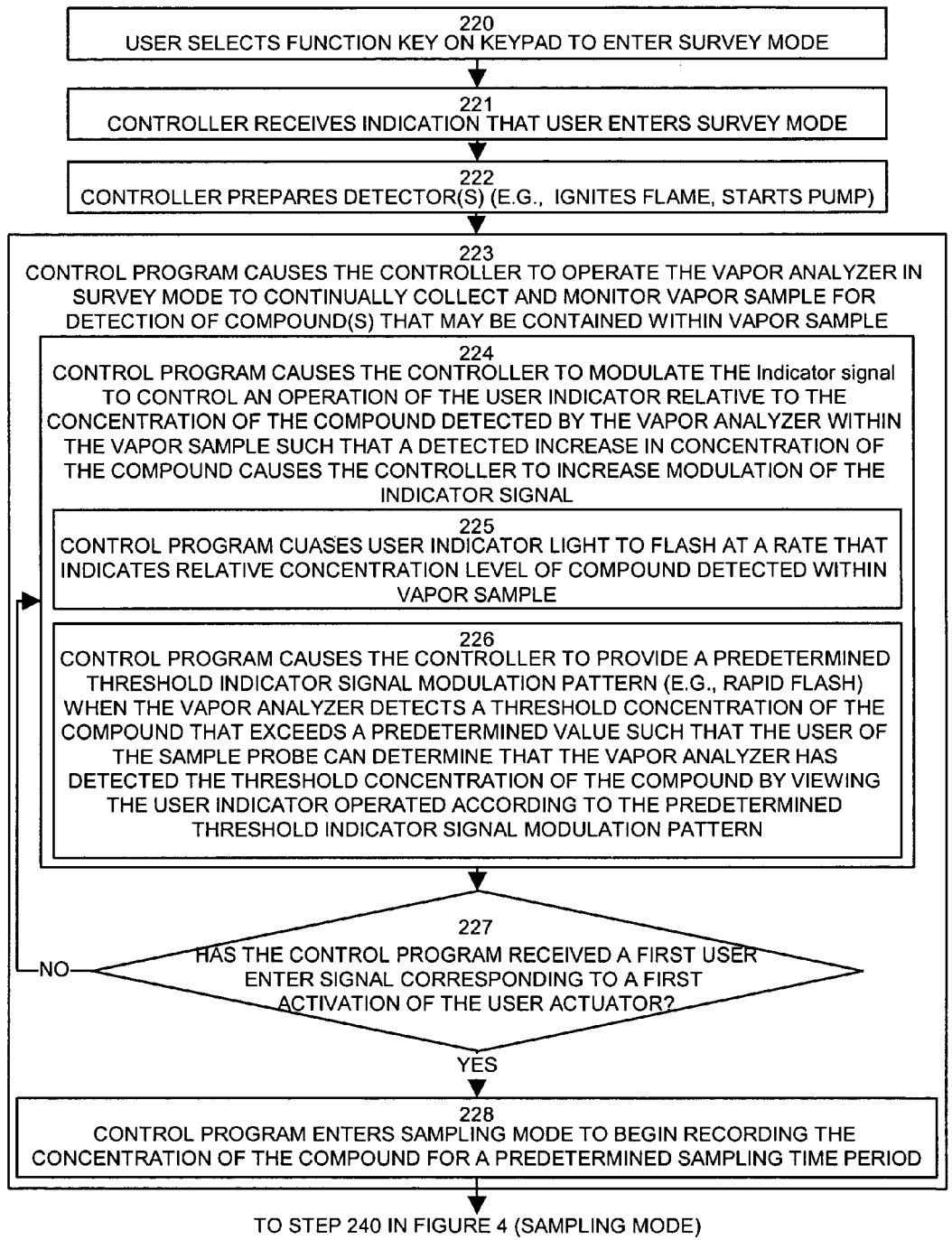
FIG. 3 is a flow chart showing processing operations of a survey mode performed by a control program operating in a controller in a vapor analysis system configured according to one embodiment of the invention.

FIG. 3 is a flow chart of processing steps that a control program 122 performs according to one embodiment of the invention in order to provide survey mode processing as explained herein.

In step 220, the user enters the survey mode, for example, by selecting a special function key 173 or selecting a menu item from the display 172 on the data entry device 170 that initializes the vapor analysis system 100 to begin to perform in survey mode.

In step 221, the controller 120 operating the control program 122 receives the indication that the user desires to enter into the survey mode via activation of the corresponding function key 173.

In response, in step 222 the control program 122 causes the controller 120 to ignite a flame in a flame ionization vapor detector 130-1 and turn on the pump 140 that will be used for collection, analysis and detection of compounds that may be contained within vapor samples 103 that are to be collected by the vapor analysis system 100. Note that by providing a special function key 173 that initiates survey mode and performs that task of igniting the flame for the vapor detector 130, the user does not have to interact with the system housing 110 to manually ignite this flame.

Next, in step 223, the control program 122 causes the controller 120 to operate the vapor analyzer 130 (one or more) in the survey mode to continually collect and monitor the vapor samples 103 for the detection of compounds such as hydrocarbons that may be contained within the vapor samples 103. Sub-steps 224 through 227 show repetitive processing of the control program 122 while in survey mode.

In step 224, the control program causes the controller 120 to modulate the indicator signal 121 to control operation of the user indicator 158 relative to the concentration level of the compound detected by the vapor analyzer 130 within the vapor samples 103 such that the detected increasing concentration of the compound causes the controller to increase modulation of the indicator signal. Likewise, a detect decrease can decrease the modulation frequency of the user indicator 158.

As shown in sub-step 225, if the user indicator 158 is a light pipe disposed around a perimeter of the probe housing 151, the control program can flash the user indicator light 158 at a rate that indicates relative concentration levels of the compound detected with the vapor samples 103.

In addition, as shown in sub-step 226, the control program 122 can further cause the controller 110 to provide a predetermined threshold indicator signal modulation pattern such as a rapid flash or a bright or high-intensity flash or a special beeping signal when the vapor analyzer 132 detects a threshold concentration or level of the compound that exceeds a predetermined value (e.g., as defined in the route entry database record associated with the leak point 105 currently being monitored) so that the user maneuvering the sample probe 150 near the leak point 105 can determine that the vapor analyzer has detected a threshold concentration of the compound by viewing the user indicator 158 (or by hearing the threshold tone) operated according to the predetermined threshold indicator signal modulation pattern. By allowing the user to configure route entry record fields with threshold or minimum concentration levels, if the detected compound concentration level exceeds this threshold value, the control program 122 can provide the threshold indicator signal modulation pattern 121 to the user indicator 158 to indicate to the user that the sample area being monitored has a threshold level of detected compound that exceeds the predetermined leak definition and thus chances are high that the leak point 105 is leaking the detected compound into the atmosphere. For some leak points, the measured value of a compound may be in excess of ambient air levels, but no action may be required by the user unless the leak exceeds the leak definition specified for the route entry for that leak point.

In step 227, the control program 122 determines if it has received a first user enter signal 123 from activation of the user actuator 156 on the sample probe 150. If the control program does not detect a first activation of the user actuator 156, then steps 224 through 226 are again performed in order to continue to monitor and collect vapor samples 103 for detection of a compound and to continually display the relative concentration of this compound by modulation of the user indicator 158.

In step 227, if the control program 122 senses that the user holding the sample probe 150 has activated the user actuator 156, it proceeds to step 228 at which point the control program 122 enters a sampling mode to begin recording the concentration of the compound currently being detected for a predetermined testing time period (as will be explained shortly with respect to FIG. 4).

Prior to discussion of the sampling mode, a brief hypothetical example of operation of the vapor analysis system 100 performing in the survey mode will now be provided. In this example, consider a situation in which the user approaches a particular leak point 105 while the vapor analysis system 100 is operating in survey mode. In this state, the control program 122 is continually collecting vapor samples 103 from air surrounding the sample probe tip 152-1. The control program 122 is able to continually receive a concentration level 132 from the vapor analyzer 130 and is able to assert the indicator signal 121 that is sent to the sample probe 150 to cause the multi-directional user indicator 158 (e.g., the light pipe or a speaker) on or built into the sample probe to provide the multi-directional user stimulus (e.g., a flashing pattern of the light on the circumference of the probe housing 151-1 or a beeping tone) according to the modulated level of the indicator signal 121. When the tip 152-1 is not near the leak point 105, it is collecting ambient air that may contain some trace levels of a particular hydrocarbon compound that the vapor analyzer 130 is capable of detecting. The control program 122 receives this ambient compound detection value as a concentration level 132. Using this concentration level 132, the control program can either allow a concentration indication signal 121 to be sent to the user indicator 158 that reflects the ambient level of the compound in the surrounding air of the probe tip 152-1, or, using the minimum concentration level field value defined in the current route entry record for the current leak point (i.e., the next leak point to be tested that the user is currently approaching), the control program 122 can choose to mask any concentration signal 132 below the minimum value for the current route entry record so that the user indicator 158 does not flash or beep for ambient low levels of the compound. However, the control program can provide a periodic pulse concentration indicator signal 121 to occasionally flash or beep the user indicator 158 (e.g., every two seconds) to let the user know the device is working properly and is in the survey mode.

As the user moves the sample probe tip 152 closer and closer to sample leak point 105 (e.g., a leaking valve) and into an area that contains more and more concentrated levels of a specific compound, the vapor analyzer 130 will detect higher and higher concentration levels of a compound. Once the compound concentration level 132 exceeds a minimum defined value in the route entry record, the vapor analyzer will produce and send a correspondingly higher and higher concentration level 132 to the controller 120 that indicates this increasing level of compound(s) detected within the vapor sample 103. In response, once the minimum level is reached or exceeded, the control program 122 can continually modify the indicator signal modulation level, pattern or setting of the monitor mode indicator signal 121, such as by increasing its frequency rate, so as to control the user indicator 158 to provide a feedback signal (i.e., a faster and faster flashing light or beeping pattern) to the user to indicate to the user that the sample probe 150 is being moved into an area of increasing concentration of the compound.

Specifically, the control program 122 can, for example, cause the user indicator 158 to flash at an increasingly rapid rate as the user moves the sample probe 150 to areas of higher and higher compound concentration. The user does not need to view a concentration level on the display 172 of the keypad 170 that may be difficult to access and/or see or view when testing leak point sample areas that are difficult to reach. Instead, the user can continually view the flashing user indicator 158 on the sample probe and/or listen to an increasing beeping or tone frequency and/or feel an increasing vibration in order to determine when the sample probe tip 152-1 is positioned at the highest relative concentration of the compound being detected by the vapor analyzer 130. To find this highest concentration position near a leak point, the user may move the sample probe tip 152-1 around a perimeter of a valve or flange that may be leaking fugitive emissions of a particular hydrocarbon compound while watching the modulated user indicator. Since this indicator 158 is disposed around the entire perimeter of the sample probe housing, the user can easily view it from most possible handling positions.

At the specific location of the highest concentration, the user indicator 158 will be flashing or beeping at the most rapid rate (or may appear to be continually on), as perceived by the user holding the sample probe 150. At this location, the user can then depress the user actuator 156 in order to cause the control program 122 to transition from the survey mode in step 202 to a sampling mode in step 205 as explained next with respect to the flow chart of processing steps in FIG. 4.

Figure 4:
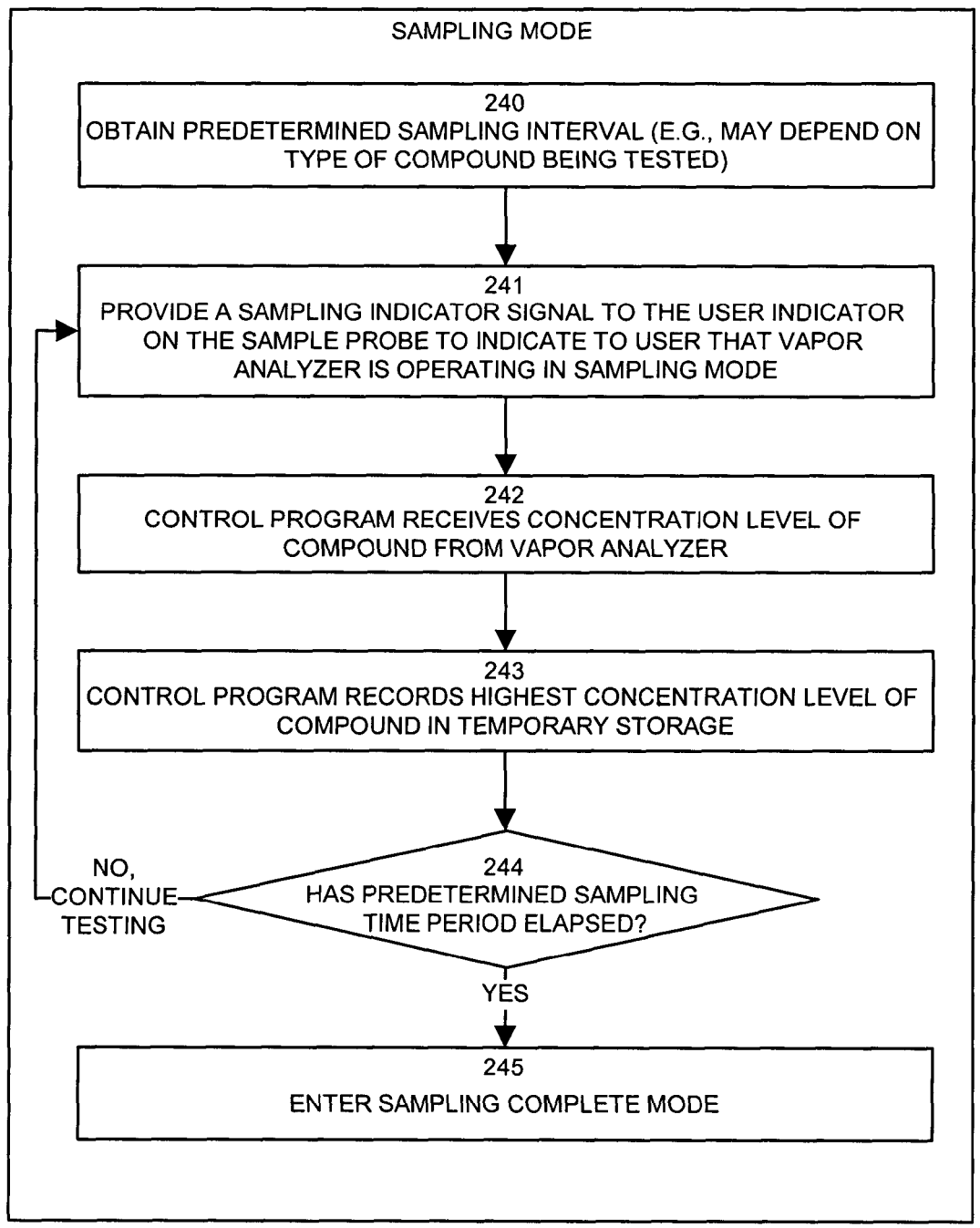
FIG. 4 is a flow chart showing processing operations of a sampling mode performed by a control program operating in a controller in a vapor analysis system configured according to one embodiment of the invention.

FIG. 4 is a flow chart of processing steps that the control program 122 performs to carry out operation of a sampling mode in accordance with one example embodiment of the invention. Entry into sampling mode occurs when the user activates the sample probe in survey mode.

In step 240, in one embodiment of the invention, the control program obtains a predetermined testing interval or test time period from the route entry database record associated with the current leak point 105. As explained briefly above, the route list 185 comprises a series of route entry records each associated with a specific respective leak point 105. Upon entry to survey mode for the first time, the control program 122 assumes that the user is monitoring a sample area associated with a first leak point 105. Each cycle that transitions from survey mode to sampling mode to sampling complete mode and then back to survey mode occurs for sequentially listed route entries in the route list 185. Also as discussed above, each route entry record can define the predetermined testing time period or interval that indicates how long the controller 120 is to operate the vapor analyzer to perform detection of a specific compound that may be leaking from the current leak point associated with the current route entry in the route list 185. Accordingly, in step 240, the control program obtains the predetermined testing interval from the appropriate route entry record corresponding to the current leak point (e.g., the first route entry record for the first leak point, second record for the second leak point, etc.). For many compounds, a test time interval of seven seconds is sufficient for the vapor analyzer to accurately measure the concentration level 132 of the compound in the vapor sample 103. However, this test or sampling time period may be varied to be greater than or less than seven seconds. In addition, since embodiments of the invention allow a user to select a test time interval for each leak point (i.e., by programming this information into the route entry record for this leak point), leak points that are difficult to test or exist in poor test conditions, such as in windy or turbulent air flow areas, can have their test time intervals increased to provide for more accurate testing of these leak points. It is to be understood that step 240 is an optional operation and that in other embodiments of the invention, the same test time interval is applied to all test points and thus each leak point is tested with the same interval. This interval may be defined in the database and can be adjustable.

Next, in step 241 the control program 122 provides a testing indicator signal 121 to the user indicator 158 on the sample probe 150 in order to indicate to the user that the vapor analyzer 130 is operating in sampling mode to perform compound detection within the vapor samples 103. In other words, in step 241, after the user operates the user actuator 156 to transition from survey mode to sampling mode, the control program 122 provides a dedicated testing indicator signal 121 to modulate the user indicator 158 to let the user know that testing is in progress. This "testing-in-progress" signal may be, for example, an alternating on and off signal using one second intervals between on and off, a steady on signal, or some other easily identifiable pattern that is different than the monitoring concentration indicator signal modulation pattern. Alternatively, during sampling mode, the indicator can be controlled to modulate according to the current detected level of concentration and thus the user in this embodiment is provided with no special modulation pattern to indicate that survey mode is taking place.

In step 242, the control program 122 receives a current detected concentration level 132 of a compound from the vapor analyzer 130. It is to be understood that this example is explained with respect to the detection of a single compound within the vapor samples 103 and that this is not meant to be limiting to embodiments of the invention. In alternative embodiments of the invention, multiple concentration levels 132 of different compounds that the vapor analyzer(s) 130-1 and/or 130-2 detect may be provided to the controller 120 for reception by the control program 122. In such cases, there might be two test time intervals defined in the route entry record, one for each of the two vapor analyzers 130-1 and 130-2.

In step 243, the control program 122 records the highest (and possibly the lowest and average) concentration level(s) of the detected compound(s) within a temporary storage area. As noted above, if embodiments of the invention support detection of different compounds (e.g., using a response factor that is customized for each compound), a corresponding respective concentration level 132 can be temporarily stored for each of the different detected compounds by one or more vapor analyzers 130. It is to be understood that detection of different concentration levels of different compounds is not required by embodiments of the invention, and that single compound detection is also contemplated in embodiments of the invention.

In step 244 the control program determines if the predetermined testing time period has elapsed. If there are two test time periods defined in the route entry record for this leak point 105 for detection of two different compounds, the longer of the two test time periods can be used in step 244. If the testing time period has not elapsed, the control program 122 continues testing and processing returns to step 241. In this manner, the control program 122 continually receives a concentration signal(s) 132 from the vapor analyzer(s) 130 in order to temporarily record or store the highest concentration level(s) detected of a specific compound or compound(s) for the duration of the testing time period(s), such as a seven second test time window or interval. In addition, during this test time, the control program 122 provides the testing indicator signal 121 in order to modulate the user indicator 158 to notify the user that testing is in progress and that the user preferably should maintain the positioning of the sample probe 150 such that the sample probe tip 152-1 is located in the same general proximity of the sample area for the leak point 105 during the entire duration of the testing time period. As noted above, in alternative embodiments, there may be no special testing indicator signal during the testing time period and the modulation signal 121 can simply supply the current concentration level.

After the testing time period has elapsed, the control program processing proceeds to step 245 at which point the control program 122 enters a sampling complete mode (step 207 in FIG. 2). Details of processing associated with sampling complete mode according to one embodiment of the invention will now be explained with respect to the flow chart of processing steps illustrated in FIG. 5.

Figure 5:
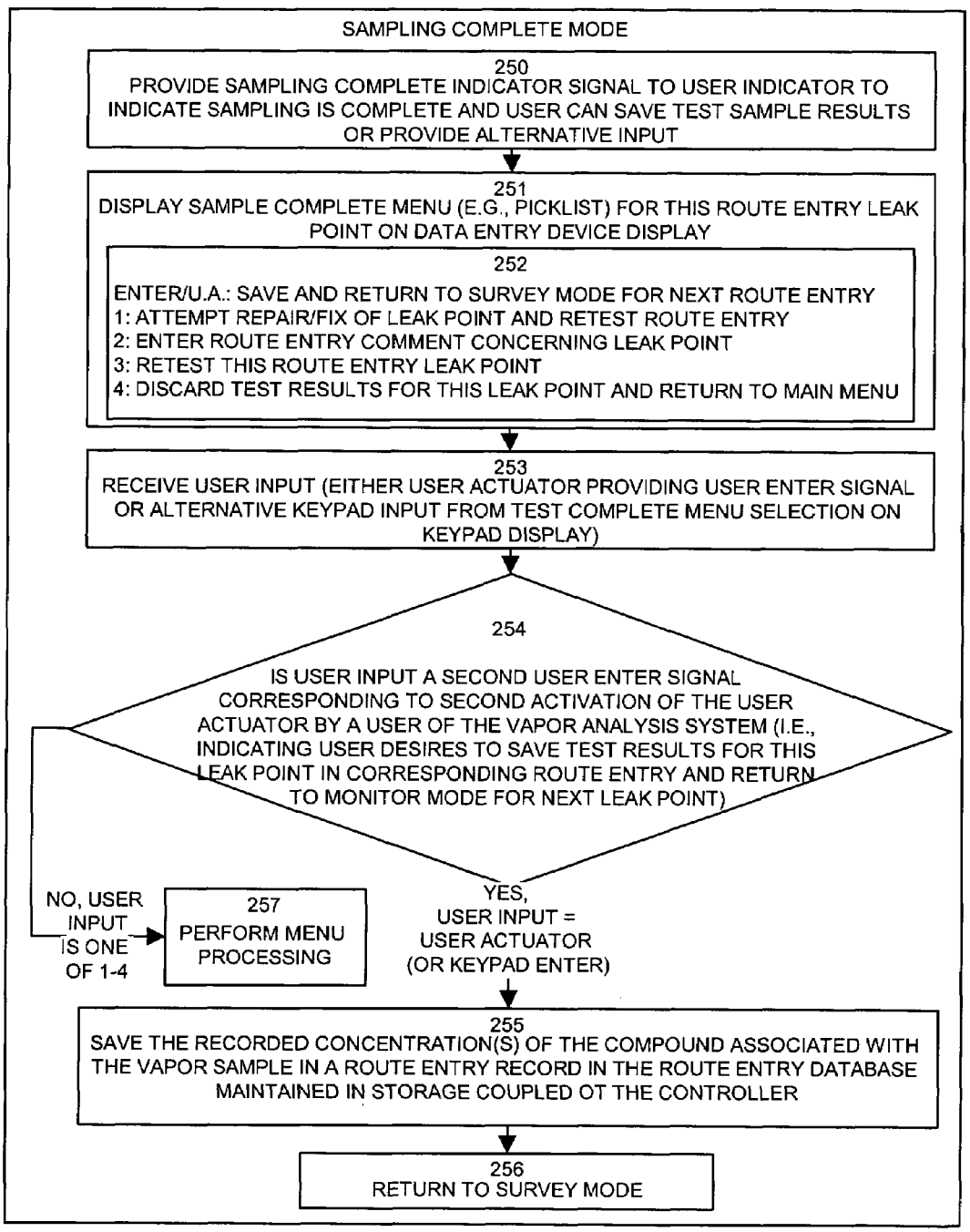
FIG. 5 is a flow chart showing processing operations of a sampling complete mode performed by a control program operating in a controller in a vapor analysis system configured according to one embodiment of the invention.

FIG. 5 is a flow chart of processing steps that a control program 122 performs to provide a sampling complete mode in accordance with one example embodiment of the invention.

In step 250, the control program 122 provides a sampling complete indicator signal 121 to the user indicator 158 within the sample probe 150 in order to indicate that sampling is completed for the most recently collected vapor samples 103 and that the user at this point in time can either save the test results or can provide alternative input by operating the data entry device 170. The sampling complete indicator signal 121 may be, for example, a continuously "on" indicator signal 121 that continuously activates the user indicator 158 in order to indicate to the user that sampling is now complete. Alternatively, the testing complete indicator signal 121 can be modulated in one pattern to indicate no leak was detected, or the controller 120 can modulate the testing complete signal 121 in another pattern to indicate to the user that a leak was detected. If the user indicator 158 is a light pipe, the testing indicator signal can, for example, continuously maintain the light pipe in an illuminated or constantly on condition if a leak was detected. If the user indicator 158 is an audible notification mechanism such as a speaker, the control program 122 can provide a constant sampling complete tone (via indication signal 121) that a speaker transmits so that the user can quickly conclude the sampling is now complete. Note that the control program 122 can modulate the sampling complete indicator signal 121 in a manner that is different than the sampling indicator signal to allow the user to determine when the sampling time period has elapsed. Also, the sampling complete pattern can be different depending upon whether or not a leak was detected.

In step 251, the control program 122 interoperates with the data entry device 170 in order to display a sampling complete menu such as a pick list associated with the current route entry leak point 105 on the data entry device display 172. An example of this pick list menu is illustrated in sub-step 252.

Specifically, as shown by the menu selection choices for pick list entries in sub-step 252, the user is able to press the enter key 174 on the data entry device 170 or alternatively is able to operate the user actuator 156 in order to generate a user enter signal 123. As shown by the menu in step 252, this user action (i.e., pressing enter or operating the user actuator) causes the control program 122 to save the highest (and/or lowest and average) recorded concentration level in the particular route entry associated with the current leak point and return processing to survey mode (step 202 in FIG. 2) in order to begin monitoring another vapor sample 103 for the next route entry associated with another leak point to be tested for the presence of a specific compound. Alternatively, other choices that the user may provide at this time are provided by selection of numeric keys 171 in the data entry device (or by corresponding special function keys 173 on the keypad 170).

Specifically, if the user selects numeric choice 1 in the menu in sub-step 252, the user can indicate that he or she attempted to repair or fix the leak point 105 and desires to retest this leak point. If the user selects user input choice 2, the user can indicate to the control program 122 that he or she desires to input a route entry comment concerning this particular leak point 105 that is to be saved within the comment field associated with the route entry record for the currently point. In this manner, in addition to recording the highest concentration level of the compound, the user is able to provide additional information concerning this leak point. This can be valuable, for example, to allow the user performing the testing to address concerns of equipment at a particular leak point, such as a valve that may not be leaking yet, but that appears to be significantly corroded and should, based on the observation of the user, be replaced preemptively prior to a leak occurring in the future. By selecting choice 3 from the sampling complete menu shown in sub-step 252, the user can indicate that he or she desires to sample this particular route entry leak point 105. Finally, in this example, if the user selects user input choice 4 in the menu shown in sub-step 252, the user can elect to discard the test results for this particular leak point 105 and return to the main menu. It is to be understood that the example menu choices illustrated in sub-step 252 for the sampling complete menu are shown as examples only to illustrate hypothetical pick list menu items according to one embodiment of the invention.

After displaying the sampling complete menu on the display 172 of the data entry device 170, the control program processing proceeds to step 253.

In step 253 the control program 122 receives user input either in the form of a user enter signal 123 provided by a user operating the user actuator 156 on the sample probe 150 or alternatively, from the user providing input using the data entry device 170. As noted above, in one embodiment of the invention, operation of the user activator 156 provides a user enter signal 123 that is equivalent from the perspective of the control program 122 to a user enter signal 123 that is produced if the user depresses the enter key 174 on the data entry device 170. In other words, operation of the user actuator 156 is equivalent to the user pressing enter key 174. After receiving user input in step 253, control program processing proceeds to step 254.

In step 254, the control program 122 determines if the user input is a second user enter signal 123 (the first user enter signal being received in the survey mode to begin the sampling process) corresponding to another activation of the user actuator 156 (or activation of the enter key 174, which is an equivalent) by a user of the vapor analysis system 100. If the user provides this second activation of the user actuator 156 within the sampling complete mode, this indicates to the control program 122 that the user desires to save the current temporarily recorded concentration signal 132 for this particular leak point 105 within a corresponding field of the route entry record in the route entry list 185 of the route entry database 180. This action also indicates to the control program 122 that the user further desires to return to survey mode in order to begin testing a vapor sample at the next leak point 105. Assume for this example discussion that the user input is a second activation of the user actuator 156 and thus processing proceeds to step 255.

In step 255, the control program 122 saves the highest, lowest and/or average temporarily recorded concentration levels 132 of the compound that was recorded during the sampling mode previously described with respect to FIG. 4 associated with the vapor samples 103 within a route entry record in the route entry database 180 (i.e., in the route list 185) maintained in the storage device 182 coupled to the controller 120. In this manner, in sampling complete mode, if the user input corresponds to operation or activation of the user actuator 156, the control program stores the highest record concentration level for the leak point just tested.

Thereafter, in step 256 the control program 122 reenters survey mode to begin Sampling for a concentration level of the compound associated with the next leak point defined in the route list 185. In this manner, the control program causes the controller to repeat the processing operations of operating the vapor analyzer in survey mode while providing the modulated indicator signal 121 to the user indicator to modulate operation of the user indicator to indicate to the user of the vapor analysis system the relative concentration of the compound within the vapor sample, then receiving the first user enter signal to enter the sampling mode to record the concentration of the compound in the vapor sample during the predetermined sampling period (and provide a sampling indicator signal 121 to indicate operation in sampling mode) and then to enter a sampling complete mode and receiving the second user enter signal causing the controller to save the recoded concentration of the compound and re-enter the survey mode. This process can be repeated for a plurality of route entry records in the route entry database, such that a user of the vapor analysis system can perform testing of a plurality of leak points, each corresponding to a route entry in the route entry database 180 (i.e., in the route list 185). This entire process can be repeated over and over by only operating the user actuator 156 on the sample probe 150 and by viewing or listening to, or otherwise sensing a signal from, the user indicator 158 on the sample probe.

Returning attention to step 254, if the control program 122 determines that the user input is neither activation of the user actuator 156 nor operation of the enter key 174, processing proceeds to step 257 in order to process test complete menu processing as explained above for choices 1 through 4 of the test complete menu shown in sub-step 252. That is, control program 122 can proceed to perform processing operations associated with each of these user selectable choices. As an example, if the user in step 257 selects choice 1 in order to attempt a repair or fix of a leak point for this route entry, the control program 122 can, for example, present another pick list with a selection of choice regarding possible techniques for fixing this leak point 105. If the user selects pick list menu choice 2, the control program can prompt the user, on the display 172, to enter a comment, such as how the user attempted to fix the leak point 105.

As noted above, in another alternative embodiment of the invention, selection of pick list menu choices can cause the control program 122 to present additional pick lists or sub-menus. As an example, if the user selects choice 1 to indicate to the control program 122 that the user desires to perform a repair operation on a leak point whose leak of a compound exceeds a predetermined threshold, the control program 122 can display a secondary pick list or sub-menu allowing the user to input the process by which that user attempted to perform a repair such as by tightening a valve nut or resealing a pipe flange by way of example. Other menu selections can cause the control program 122 to present additional pick lists in the form of sub-menus that can further prompt the user to enter additional information or to guide the user through various processing paths associated with user interaction with the control program 122. In this manner, embodiments of the invention allow an operator or administrator of the vapor analysis system 100 to design a series of sub-menus within route entry records. The sub menus are referred to herein as pick lists that can prompt the user with customized menus and the ability to input customized data associated with particular leak points 105. The control program 122 is configured to traverse route entry records that define pick lists and for each pick list menu choice, the route entry can specify either a pointer to another pick list, or can define a data value to be saved that corresponds to the user's pick list menu selection choice and/or can indicate an operating mode to enter into (typically the survey mode). As an example, if a route entry contains a pick list menu definition that gets displayed during the sampling complete mode, this pick list might contain three menu choices. The first choice might be to re-test a leak point. Selection of this first choice would cause the control program to discard the recorded concentration from the just completed sampling mode and to re-enter sampling mode again. Other choices might direct the control program 122 to display another pick list of menu choices. In general then, each pick list choice in a route entry record can include additional information to properly direct the control program 122 to perform an appropriate action or actions. As an example, such additional information for each pick list choice can instruct the control program 122 to, for example, enter a certain operating mode (e.g., survey mode or sampling mode), whether or not the control program 122 should save the most recently recorded testing results in a proper route entry field, and whether or not the control program 122 should save the most user's pick list menu choice. Those skilled in the art will understand that there can be many variations of this functionality that are considered to be part of the functionality provided by embodiments of the invention and that the aforementioned examples are not intended to be limiting in nature.

Based on the foregoing description, in the sampling complete mode the control program 122 provides a testing complete indicator signal 121 to the user indicator 158 on the sample probe 150 to indicate to the user that the testing is complete for the route entry leak point 105. The testing complete indicator signal 121 can, for example, maintain the user indicator 158 in a steadily on state to indicate to the user that testing is complete. At this point (i.e., steps 253/254), the user can determine if he or she is satisfied that the sample probe tip 152-1 was appropriately positioned during the sampling mode and if so, the user can again operate the user actuator 156 (i.e., the second activation) to send another user enter signal 123 to the control program to indicate to the control program 122 that the user is satisfied with the testing procedure. In response to this second operation of the user actuator 156 when the control program 122 is in the sampling complete mode, the control program 122 can save the recorded concentration level 132 into the appropriate route list entry testing results field in the route list 185 corresponding to the leak point 105 for which testing was performed.

In other words, the testing complete indicator signal 121 operates the user indicator 158 to provide a cue to the user to make a decision as to whether or not the user desires to save the test results in the route list 185. If the user is comfortable with the testing procedure as it was performed (e.g., the user held the probe tip in the proper area), the user can depress the user indicator 156 that causes the control program 122 to save the highest recorded concentration level of the compound(s) as a final test result within the route entry record for this leak point 105. In addition, after saving the test result concentration level 132, the control program 122 can transition from the sampling complete mode back to the survey mode which causes the pump 140 and vapor analyzer 130 to again begin collecting a new vapor sample 103 for testing of the next leak point 105 defined by the next route entry in the route list 185.

At this point in time, the control program 122 can enter survey mode again to begin another sequence of continually collecting a vapor sample 103 for analysis by a vapor analyzer 130. The user can then begin approaching (e.g., walking to) the next leak point sample area corresponding to the next route entry in the route list 185. The aforementioned processing then repeats itself again for the next leak point defined by the next route entry in the route list 185.

Using the aforementioned sequence of transitions from survey mode to sampling mode, then to sampling complete mode and back to survey mode, a user of the vapor analysis system 100 configured according to embodiments of the invention can perform testing of multiple leak points 105 defined by successive route entries in the route list 185 by operating the user actuator 156 alone and by viewing/listening to stimulus patterns produced by the user indicator 158 as a result of the control program 122 modulation of the indicator signal 121 during the various operating modes. Assuming a user is satisfied with testing procedures and placement of sample probe tip 152-1 at each of the leak point sample areas 105, the user does not need to frequently interact with or operate the data entry keypad device 170 during typical testing operations for many successively tested leak points. Embodiments of the invention thus significantly decrease total time required to perform testing of a sequence of individual leak points and therefore improve overall user productivity when using the vapor analysis system 100.

Those skilled in the art will understand that there can be many variations made to the embodiments explained above while still achieving the same objective of those embodiments and the invention in general.

For example, since a user of the vapor analysis system can perform testing of many leak points using only the user actuator 156 on the sample probe 150, the data entry device 170 is not required by all embodiments of the invention. The data entry device 170 is therefore optional, and if included provides the additional functionality related to allowing user customizable pick lists and other features explained in relation to the data entry device 170. Other alternative arrangements of embodiments of the invention provide that the communications channels 163 and 165 between controller 120 and both the data entry device 170 and the sample probe 150 are wireless communications channels. This allows the keypad 170 to be physically separate from the system housing 110, thus avoiding a user having to deal with cable management issues. In addition, other variations to embodiments of the invention provide that the patterns of modulation for the indicator signal 121 for each operating mode are of any suitable nature so as to convey to the user the various operating modes. Embodiments of the invention are not limited to the patterns described in the above examples.

In another alternative embodiment, the control program 122 allows the route list 185 to be loaded into the storage 182 via operation of the stationary computer system 190. In addition, a data manager within the control program 122 allows a user to edit and also add new route entries while in the field. During the process of downloading the collected leak point data 181 after using the system 100 in the field, the modified or newly created entries can be transferred back to the stationary computer system 190 at the end of the monitoring process (e.g., at the end of a day in the field) in order to update the master data of the software 191 maintained in the stationary computer system 190. In this manner, by allowing a user to create new route entries "on the fly" while in the field, new leak points for additional equipment that might have been recently installed can be added into the original set of leak points defined in the original route list 185. can guide a user through predefined types of pick list selections to indicate what the new leak point is (e.g., a valve, manifold, etc.). This avoids the user from having to type in large amounts of data to describe the new leak point. The user may thereafter edit the selected data to even further customize the newly defined leak point.

These and other variations are intended to be covered by the scope of this invention. As such, the foregoing description of embodiments of the invention is not intended to be limiting.

What is claimed is:

1. A vapor analysis system comprising:
   a vapor analyzer capable of collecting and analyzing a vapor sample for detection of a compound that may be contained within the vapor sample;
   a controller coupled to the vapor analyzer, the controller programmed to produce an indicator signal indicative of a relative concentration of the compound detected by the vapor analyzer within the vapor sample; and
   a sample probe including:
      a housing supporting a vapor channel through which the vapor sample is collected;
      a vapor cable coupling the vapor channel to the vapor analyzer to allow collection and channeling of the vapor sample to the vapor analyzer for analysis and detection of a compound that may be contained within the vapor sample; and
      a multi-dimensional user indicator, the user indicator in communication with the controller to receive and operate in response to the indicator signal to indicate the relative concentration of the compound detected within the vapor sample for presentation via a multi-directional stimulus to a user of the vapor analysis system;
   wherein the sample probe further comprises:
   a user actuator coupled via a data communications channel to the controller to provide a user enter signal to the controller based on operation of the user actuator by a user of the vapor analysis system in order to control operation of a control program operating within the controller;
   the control program causing the controller to operate the vapor analyzer in a survey mode to continually collect and monitor the vapor sample for detection of the compound that may be contained within the vapor sample;
   the control program causing the controller to modulate the indicator signal to control an operation of the user indicator relative to the concentration of the compound detected by the vapor analyzer within the vapor sample such that a detected change in concentration of the compound causes the controller to change modulation of the indicator signal; and
   the control program causing the controller to provide a predetermined threshold indicator signal modulation pattern when the vapor analyzer detects a threshold concentration of the compound that exceeds a predetermined value such that the user of the sample probe can determine from a multi-directional stimulus of the user indicator that the vapor analyzer has detected the threshold concentration of the compound by viewing the user indicator operated according to the predetermined threshold indicator signal modulation pattern; wherein:
   during the survey mode, the control program receives a first user enter signal corresponding to a first activation of the user actuator by the user of the vapor analysis system;
   in response to the first user enter signal, the control program enters a sampling mode to begin recording the concentration of the compound that may be contained within the vapor sample for a predetermined testing time period, and during the sampling mode, the control program provides a testing complete indicator signal modulation pattern to modulate the user indicator on the sample probe to indicate to the user that the control program is operating in the sampling mode; and
   after the predetermined sampling time period has elapsed, the control program enters a sampling complete mode and providing a sampling complete indicator signal modulation pattern to modulate the user indicator on the sample probe to indicate to the user that the sampling mode is complete;
   in the sampling complete mode, the control program receives a second user enter signal corresponding to a second activation of the user actuator by the user of the vapor analysis system; and
   in response to the second user enter signal, the control program causes the controller to:
      i) save the recorded concentration of the compound associated with the vapor sample in a leak data route entry record of a route entry database maintained in a storage device coupled to the controller, the route entry record corresponding to a leak point near which the user operated the sample probe to collect the vapor sample from which the concentration of the compound was detected and recorded; and
      ii) re-enter the survey mode to begin collecting a vapor sample again for a next leak point defined by a next route entry record in the route entry database;
   wherein the control program causes the controller to repeat the processing operations of:
      operating the vapor analyzer in the survey mode;
      receiving the first user enter signal in survey mode to cause operation of the vapor analyzer in the sampling mode for the predetermined sampling period; and
      upon expiration of the predetermined testing period, operating the vapor analyzer in the sampling complete mode and receiving the second user enter signal causing the controller to save the recorded concentration of the compound and re-enter the survey mode;
      for a plurality of route entry records in the route entry database, such that a user of the vapor analysis system can perform testing of a plurality of leak points, each corresponding to a route entry in the route entry database, by only operating the user actuator on the sample probe and by sensing the multi-directional stimulus of the user indicator on the sample probe to determine an operating mode of the control program; and
      wherein the user indicator comprises a light pipe disposed around a perimeter of the housing of the sample probe, the controller modulating the indicator signal to control an intensity of the light pipe relative to the concentration of the compound detected by the vapor analyzer within the vapor sample to visually indicate via light, to the user of the vapor analysis system:
   i) operation of the control program in survey mode and sampling mode;
   ii) the relative concentration of the compound detected by the vapor analyzer in the vapor sample;
   iii) when the vapor analyzer has detected the threshold concentration that exceeds a predetermined value such that the user of the sample probe can determine that the vapor analyzer has detected the threshold concentration of the compound by viewing light produced by the user indicator operated according to the predetermined threshold indicator signal modulation pattern.

2. The vapor analysis system of claim 1 further including a system housing enclosing the controller and the vapor analyzer, and wherein the user indicator comprises an audible transducer disposed in at least one of the housing of the sample probe and the system housing, the controller modulating the indicator signal to control an intensity of the audible transducer relative to the concentration of the compound detected by the vapor analyzer within the vapor sample to audibly indicate via sound, to the user of the vapor analysis system:
   i) operation of the control program in survey mode and sampling mode;
   ii) the relative concentration of the compound detected by the vapor analyzer in the vapor sample;
   ii) when the vapor analyzer has detected the threshold concentration that exceeds a predetermined value such that the user of the sample probe can determine that the vapor analyzer has detected the threshold concentration of the compound by listening to the sound produced by the user indicator operated according to the predetermined threshold indicator signal modulation pattern.

3. The vapor analysis system of claim 1 wherein the sample probe includes a flexible sample probe tip coupled to a first end of the vapor channel, the flexible sample probe tip being manually positionable by the user along an sample axis that is different that a central axis of the vapor channel within the sample probe.

4. The vapor analysis system of claim 1 wherein the vapor cable has an input end that can be coupled and decoupled from an output end of the vapor channel of the sample probe and has an output end that can be coupled and decoupled from an interface of the vapor analysis system that channels the vapor sample to the vapor analyzer, such that the vapor cable can be replaced in an event of contamination or damage.

5. The vapor analysis system of claim 1 further comprising:
   a storage device coupled to the controller, the storage device maintaining:
      i) a control program that the controller can execute to cause the controller to perform processing operations associated with operation of the vapor analysis system including controlling operation of the vapor analyzer to test for the existence of the compound in the vapor sample;
      ii) a route entry database containing a plurality of user-defined route entry records, each route entry record corresponding to a leak point at which the user of the vapor analysis system operates the sample probe of the vapor analysis system to test for the presence of a compound in a respective vapor sample collected at that vapor testing point; and
      each route entry record including at least one route entry field that has a field size and field type that can be changed by the user to correspond to a variety of different field sizes and field types required by different vapor analysis software programs that can download the route entry database for post processing after collection of vapor samples for route entry records.

6. The vapor analysis system of claim 5 wherein the storage device is a removable storage device medium that, when removed from the vapor analysis system, persistently maintains the route entry database including a respective concentration level of the compound detected for each vapor sample associated with a respective route entry record corresponding to a vapor testing point.

7. The vapor analysis system of claim 5 wherein:
the control program can be remotely re-programmed using a configuration computer system coupled via an interface to the controller to allow a user of the configuration computer system to upload the control program into the memory of the vapor analysis system to allow the control program to be adapted to collect user-defined vapor analysis route entry record data associated with the concentration of the compound in a vapor sample in a route entry record format maintained in the route entry database that is compatible with vapor analysis data processing software that operates on the configuration computer system.

8. The vapor analysis system of claim 7 wherein the user of the configuration computer system can configure the control program to save route entry record data in the route entry database in a user definable field format that includes, for each route entry record, a time of vapor sample collection, a date of vapor sample collection, a concentration level of the compound that the vapor analyzer detects within the vapor sample, and a location of vapor sample collection.

9. The vapor analysis system of claim 5 further comprising:
   a data entry device in communication with the controller, the data entry device comprising:
      a set of data entry keys for user input of information into the control program operating in the controller;
      a set of special function keys that, when operated by the user, cause the control program to invoke a series of predefined instructions that control vapor analysis mechanisms within the vapor analyzer without the user having to interact with a system housing that contains the controller and the vapor analyzer; and
      a user enter key that also provides the user enter signal to the controller.

10. The vapor analysis system of claim 9 wherein:
the data entry device includes a display capable of displaying multiple rows and columns of characters to provide visual output information to the user from the controller during operation of the control program; and
wherein at least one route entry field of at least one route entry record in the route entry database includes a menu that the control program can display on the display of the data entry device, the menu defining a set of user-defined and user selectable choices associated with operation of the vapor analysis system; and
wherein during an operational mode of the control program, the control program identifying a menu associated with that operational mode and displaying the menu on the display of the data entry device during that operational mode;
the control program receiving a user selectable choice from the displayed menu and processing the user selectable choice to perform at least one of:
   i) entering a different operational mode;
   ii) saving the user selectable choice into a field of the route entry record for the leak point; and
   iii) displaying a pick list associated with the user selectable choice and awaiting selection of another user selectable choice from the pick list;
   iv) displaying user defined fields from a user defined route entry record in the route entry database; and
   v) allowing a user to edit route entry information associated with the route entry record in the route entry database to perform at least one modification of existing data in the route entry record and creation of a new route entry record.

11. The vapor analysis system of claim 10 wherein the pick list defined in a route entry record for at least one leak point is at least one of:

a leak source and repair pick list that identifies a leak source and plurality of leak point repair methods and wherein the control program displays the leaks source and repair pick list on the display of the data entry device to receive a user selectable choice corresponding to a source of a leak and a type of repair operation that the user performed on the leak point.

12. The vapor analysis system of claim 10 wherein the control program receives a comment entry command that causes the control program to prompt the user for a comment string on the display of the keypad device, the control program receiving the comment string and storing the comment string in a route entry field associated with the route entry record for the leak point.

13. The vapor analysis system of claim 1 further comprising:

a leak point identification mechanism coupled to the controller, the leak point identification mechanism providing, to the controller, leak point identification data corresponding to a location of a leak point from which the vapor sample is collected, the leak point identification data being generated by the leak point identification mechanism in the survey mode to identify the leak point, the control program operating in the controller saving the leak point identification data in a route entry record of the route entry database upon activation of the user actuator disposed on the sample probe.

14. The vapor analysis system of claim 13 wherein the leak point identification mechanism is at least one of:

a global positioning system transceiver capable of detecting a global position location value upon user activation of the user actuator and providing the global position location value as the leak point identification value to the controller for storage within the route entry associated with leak point from which the vapor sample is collected; and a radio frequency tag identification reading mechanism capable of reading a tag identity of a leak point from a radio frequency tag positioned in proximity to the leak point, and providing the tag identity as the leak point identification value to the controller for storage within the route entry associated with the leak point from which the vapor sample is collected.

15. The vapor analysis system of claim 1, wherein the multi-dimensional user indicator is a non-planar indicator disposed around a perimeter of the sample probe to produce the multi-directional stimulus for sensing by the user.

16. The vapor analysis system of claim 15, the controller is configured to produce a predetermined threshold indicator signal modulation pattern when the vapor analyzer detects a threshold concentration of the compound that exceeds a predetermined value such that the user of the sample probe can detect, based on the multi-directional stimulus as produced by the multi-dimensional indicator, that the vapor analyzer has detected the threshold concentration of the compound.

17. A vapor analysis system comprising:

a vapor analyzer capable of collecting and analyzing a vapor sample for detection of a compound that may be contained within the vapor sample;

a controller coupled to the vapor analyzer, the controller programmed to produce an indicator signal indicative of a relative concentration of the compound detected by the vapor analyzer within the vapor sample; and a sample probe including:

a housing supporting a vapor channel through which the vapor sample is collected;

a vapor cable coupling the vapor channel to the vapor analyzer to allow collection and channeling of the vapor sample to the vapor analyzer for analysis and detection of a compound that may be contained within the vapor sample; and a multi-dimensional user indicator, the user indicator in communication with the controller to receive and operate in response to the indicator signal to indicate the relative concentration of the compound detected within the vapor sample for presentation via a multi-directional stimulus to a user of the vapor analysis system wherein the sample probe includes a substance filter disposed within the vapor channel, the substance filter capable of filtering at least one substance from the vapor sample as the vapor sample is collected through the vapor channel;

wherein the substance filter includes a particulate filter trap to extract and contain particulate matter from the vapor channel as the vapor sample is collected;

wherein the substance filter includes a liquid filter trap to extract and contain liquid from the vapor channel as the vapor sample is collected;

wherein the liquid filter trap is constructed of a translucent material;

wherein the housing of the sample probe defines a liquid filter trap containment section to position and maintain the liquid filter trap within the vapor channel at a location after the substance filter in a path of vapor sample travel; and wherein the liquid filter trap containment section defines a liquid filter trap window that allows the user of the vapor analysis system to visually inspect the contents of the liquid filter trap to determine if liquid is contained within the liquid filter trap.

18. The vapor analysis system of claim 17 wherein the substance filter is removable from the sample probe.

19. A vapor analysis system comprising:

a vapor analyzer for analyzing a vapor sample to detect a compound that may be contained within the vapor sample;

a controller coupled to the vapor analyzer and operable to produce an indicator signal indicative of a relative concentration of the compound detected by the vapor analyzer;

a sample probe including (a) a vapor channel through which the vapor sample is collected and (b) a user indicator in communication with the controller, said user indicator operable to receive the indicator signal and to respond to the indicator signal by presenting to a user of the probe a multi-dimensional stimulus indicative of the relative concentration of the compound detected within the vapor sample;

a vapor cable for passing the vapor sample from the vapor channel of the sample probe to the vapor analyzer; and wherein the sample probe includes a housing containing the vapor channel, the user indicator comprises a light pipe disposed around the perimeter of a portion of said housing, and the controller is operable to modulate the level of the indicator signal so as to control the level of light emitted by the light pipe relative to the concentration of the compound detected within the vapor sample.

20. The vapor analysis system of claim 19 wherein the controller is operable to modulate the level of the indicator signal in response to changes in concentration of the compound detected within the vapor sample.

21. The vapor analysis system of claim 19, wherein the multi-dimensional stimulus indicative of the relative concentration is provided by a non-planar indicator disposed around a perimeter of the sample probe.

22. The vapor analysis system of claim 19 wherein the sample probe includes a probe housing containing the vapor channel, the user indicator comprises a speaker or audible transducer disposed on or within said housing, and the controller is operable to modulate the intensity of the indicator signal so as to control the intensity of sound emitted by the speaker or audible transducer relative to the concentration of the compound detected within the vapor sample.

23. The vapor analysis system of claim 19 further including a data storage device coupled to the controller, said data storage device operable to maintain a route entry database with data relating to a route of locations and to store data on the compounds detected within vapor samples collected at said locations.

24. The vapor analysis system of claim 23 wherein the controller includes a control program, and the sample probe includes a user actuator in data communication with the controller to enable a user to transmit a user enter signal to the controller in order to change the mode of operation of the control program.

25. The vapor analysis system of claim 24 wherein the controller and the computer program are operable in a survey mode to cause the vapor analyzer to continually analyze a vapor sample passed to it through the vapor cable and for the controller to provide an indicator signal with a predetermined threshold modulation pattern when the vapor analyzer detects a concentration of the compound that exceeds a predetermined value.

26. The vapor analysis system of claim 25 further comprising:
  a leak point identification mechanism coupled to the controller, the leak point identification mechanism operable to provide, to the controller, leak point identification data corresponding to a location of a leak point from which the vapor sample is collected, the leak point identification data being generated by the leak point identification mechanism in the survey mode to identify the leak point, the control program operable to save the leak point identification data in a route entry record of the route entry database upon activation of the user actuator.

27. The vapor analysis system of claim 26 wherein the leak point identification mechanism is at least one of:
  a global positioning system transceiver capable of detecting a global position location value upon user activation of the user actuator and providing the global position location value as the leak point identification value to the controller for storage within the route entry associated with leak point from which the vapor sample is collected; and
  a radio frequency tag identification reading mechanism capable of reading a tag identity of a leak point from a radio frequency tag positioned in proximity to the leak point, and providing the tag identity as the leak point identification value to the controller for storage within the route entry associated with the leak point from which the vapor sample is collected.

28. The vapor analysis system of claim 24 wherein the controller and the computer program are operable, in response to a first activation of the user actuator, to cause the vapor analyzer to continually analyze a vapor sample during a predetermined sampling time period and for the controller to provide an indicator signal with a predetermined sampling modulation pattern during the sampling time period and an indicator signal with a testing complete indicator signal modulation pattern at the end of the sampling time period.

29. The vapor analysis system of claim 28 wherein the controller and the computer program are operable, in response to a second activation of the user actuator, to save the recorded concentration of the compound associated with the vapor sample in said data storage device as a route entry record of the route entry database.

* * * * *